US010555995B2

(12) United States Patent
Hause et al.

(10) Patent No.: US 10,555,995 B2
(45) Date of Patent: Feb. 11, 2020

(54) PORCINE PESTVIRUS, VACCINES, AND ASSAYS

(71) Applicant: Kansas State University Research Foundation, Manhattan, KS (US)

(72) Inventors: Ben Hause, Westmoreland, KS (US); Emily Collin, Lenexa, KS (US); Ying Fang, Manhattan, KS (US); Lalitha Peddireddi, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 0 days.

(21) Appl. No.: 15/569,641

(22) PCT Filed: Apr. 29, 2016

(86) PCT No.: PCT/US2016/030210
§ 371 (c)(1),
(2) Date: Oct. 26, 2017

(87) PCT Pub. No.: WO2016/176624
PCT Pub. Date: Nov. 3, 2016

(65) Prior Publication Data
US 2018/0303926 A1    Oct. 25, 2018

Related U.S. Application Data

(60) Provisional application No. 62/155,004, filed on Apr. 30, 2015.

(51) Int. Cl.
*A61K 39/12*    (2006.01)
*C12Q 1/70*    (2006.01)
(Continued)

(52) U.S. Cl.
CPC .............. *A61K 39/12* (2013.01); *A61K 39/42* (2013.01); *A61P 31/12* (2018.01); *C12Q 1/70* (2013.01);
(Continued)

(58) Field of Classification Search
None
See application file for complete search history.

(56) References Cited

U.S. PATENT DOCUMENTS

2018/0303926 A1*    10/2018    Hause .................... A61K 39/12

FOREIGN PATENT DOCUMENTS

| WO | 2000009701 | 2/2000 |
|---|---|---|
| WO | 2015025165 | 2/2015 |

OTHER PUBLICATIONS

Hause et al. (Journal of General Virology. 2015; 96: 2994-2998).*
(Continued)

*Primary Examiner* — Shanon A. Foley
(74) *Attorney, Agent, or Firm* — Hovey Williams LLP

(57) ABSTRACT

Porcine pestivirus designated herein as atypical porcine pestivirus ("APPV") (Genbank accession no. KR011347.1). Immunogenic compositions to induce an immune response against porcine pestivirus infection in a pig are described, which APPV antigenic agents (e.g., isolated whole virus, derivatives thereof, functional fragments thereof, and combinations of the foregoing). Methods of vaccinating against porcine pestivirus infection using the immunogenic compositions are also described. The methods can be also applied for clinical research and/or study, including diagnostic methods for detecting pestivirus infection using monoclonal antibodies specifically binding to APPV epitopes.

9 Claims, 8 Drawing Sheets

Specification includes a Sequence Listing.

(51) Int. Cl.
    A61P 31/12    (2006.01)
    G01N 33/569   (2006.01)
    A61K 39/42    (2006.01)
    A61K 39/00    (2006.01)
(52) U.S. Cl.
    CPC .... *G01N 33/569* (2013.01); *A61K 2039/5252* (2013.01); *A61K 2039/5254* (2013.01); *A61K 2039/552* (2013.01)

(56) References Cited

OTHER PUBLICATIONS

Sequence alignment of instant Seq ID Nos. 1 with GenEmbl db access No. KR011347 Hause et al 2015.*
Alignment of Seq ID 1 with GenEmbl db access No. KU194229 Arruda et al 2016.*
Alignment of Seq ID 3 with Genseq db access No. BBF51883 Hyun et al 2014.*
Alignment of Seq ID 3 with Genseq db access No. BDB54330 DeGroof et al 2016.*
Alignment of Seq ID 4 with Issued_Patents No. 15253511 2015.*
Greenspan et al (Nature Biotechnology 17:936-937 (1999)).*
Tao et al. (Veterinary Microbiology. 2013; 165: 185-189).*
Soos et al. (Acta Veterinaria Hungarica. 2001; 49 (1): 17-24, abstract only).*
Jasna et al. (Acta Veterinaria (Beograd), 2007; 57 (5-6): 413-427).*
Osterhaus, Albert, et al. "Control and eradication of Classic Swine Fever in wild boar and Animal health safety of fresh meat derived from pigs vaccinated against Classic Swine Fever 2 Scientific opinions of the Panel on Animal Health and Welfare." (2007).*
The International Search Report and Written Opinion dated Nov. 15, 2016, in PCT/US2016/030210 filed Apr. 29, 2016.
Hause, Ben M. "Discovery of a novel putative atypical porcine pestivirus in pigs in the USA," Journal of General Virology, Jul. 24, 2015, pp. 2994-2998, vol. 96.
"KR011347: Porcine pestivirus 1 strain 000515 polyprotein mRNA, complete cds," GenBank, Jul. 29, 2015. pp. 1-7.
Kirkland, P.D. "Identification of a novel virus in pigs—Bungowannah virus: A possible new species of pestivirus." Science Direct, Virus Research 129, Jun. 11, 2007, pp. 26-34.
Arruda, Bailey L. "Identification of a Divergent Lineage Porcine Pestivirus in Nursing Piglets with Congenital Tremors and Reproduction of Disease following Experimental Inoculation," PLOS one, Feb. 24, 2016, vol. 11, pp. 1-12.

* cited by examiner

MARC-145 cells expressing APPV-Erns       Control MARC-145 cells

LN-APPV infection       LN-control

Fig. 3A

PORCINE PESTVIRUS, VACCINES, AND ASSAYS

CROSS-REFERENCE TO RELATED APPLICATIONS

The present application is the National Stage of International Patent Application No. PCT/US2016/030210, filed Apr. 29, 2016, which claims the priority benefit of U.S. Provisional Patent Application Ser. No. 62/155,004, filed Apr. 30, 2015, entitled PORCINE PESTVIRUS, VACCINES, AND ASSAYS, each of which is incorporated by reference in its entirety herein.

SEQUENCE LISTING

The following application contains a sequence listing in computer readable format (CRF), submitted as a text file in ASCII format entitled "47343-PCT Sequence Listing," created on Apr. 28, 2016, as 51 KB. The content of the CRF is hereby incorporated by reference.

BACKGROUND OF THE INVENTION

Field of the Invention

The present invention relates to atypical porcine pestivirus isolates, and methods of use thereof.

Description of Related Art

Species in the genus Pestivirus: bovine viral diarrhea virus type 1 (BVDV-1), bovine viral diarrhea virus type 2 (BVDV-2), classical swine fever virus (CSFV) and border disease virus (BDV), are some of the most significant pathogens affecting ruminants and swine. Clinical disease can lead to high morbidity and mortality. Host immunosuppression and persistent viremia are hallmarks of pestivirus infections. Pestiviruses cause economically significant disease in ruminants and swine.

In 2003, a divergent pestivirus, Bungowannah virus (BWV), was isolated from a farm in Australia exhibiting an outbreak of sudden death in three to four week-old pigs and increase in stillborn fetuses. Pathologically, multifocal non-suppurative myocarditis with myonecrosis was observed. Phylogenetic analysis found Bungowannah virus to be the most divergent pestivirus and antigenically it failed to react with pan-reactive pestivirus monoclonal antibodies. More recently, two novel pestiviruses were identified by next generation sequencing (NGS). Analysis of the virome from the bat species *Rhinolophus affinis* in China identified a 5 kb contig with 32% amino acid sequence identity to known pestiviruses. Metagenomic sequencing of Norway rats in New York City also identified a highly divergent pestivirus (Norway rat pestivirus, NRPV) which shared a maximum of 60% amino acid identity with known pestivirus polyproteins. These discoveries have challenged our understanding of the diversity and ecology of pestiviruses. These two newly described pestiviruses are the first identified in species outside the order *Artiodactyla* and suggest a wider pestivirus host range. Nothing is known on the ability for these viruses to cause disease.

SUMMARY OF THE INVENTION

The present invention is broadly concerned with immunogenic compositions to induce an immune response against porcine pestivirus infection in a pig. The compositions generally comprise a therapeutically-effective amount of atypical porcine pestivirus (APPV) antigenic agents dispersed in a pharmaceutically-acceptable carrier. Exemplary APPV antigenic agents are selected from the group consisting of isolated whole virus having an mRNA complementary coding sequence according to Genbank accession no. KR011347.1 (SEQ ID NO:1), derivatives thereof, functional fragments thereof, and combinations of the foregoing.

Also described herein are methods of vaccinating a pig to induce an immune response against porcine pestivirus infection. The methods generally comprise administering an immunogenic composition according to any one of the embodiments described herein to the pig.

Kits for inducing an immune response against porcine pestivirus infection in a pig are also described herein. The kit generally comprise an immunogenic composition according to any one of the embodiments described herein, and instructions for administering the composition to the pig.

The disclosure also concerns the use of an immunogenic composition according to any one of the embodiments described herein for inducing an immune response against porcine pestivirus infection in a pig.

Also described herein are methods of detecting pestivirus antigen in a biological sample. The methods generally comprise contacting a biological sample from a pig with a monoclonal antibody against the atypical porcine pestivirus (APPV) described herein. The monoclonal antibody specifically binds to an antigen of the pestivirus if present in the sample. The antibody-antigen binding, if present, can then be detected to confirm or refute pestivirus infection.

BRIEF DESCRIPTION OF THE DRAWINGS

FIG. 3A shows the detection of APPV antigen by indirect immunofluorescence assay. The top two panels show MARC-145 cells transfected with a plasmid DNA expressing pestivirus Erns protein or mock-transfected (control), as indicated, and stained with DAPI for visualizing the cell nucleus. The bottom two panels show immunofluorescent staining with DAPI in of lymph node section from formalin-fixed paraffin-embedded tissues. Tissue sections are shown from samples identified as APPV positive by qRT-PCR ("LN-APPV infection"), and from a healthy pig, identified as APPV negative by qRT-PCR ("LN-control"), as indicated. Images were taken by a confocal microscope (LSM 880, Zeiss);

DETAILED DESCRIPTION

Figure 1A:
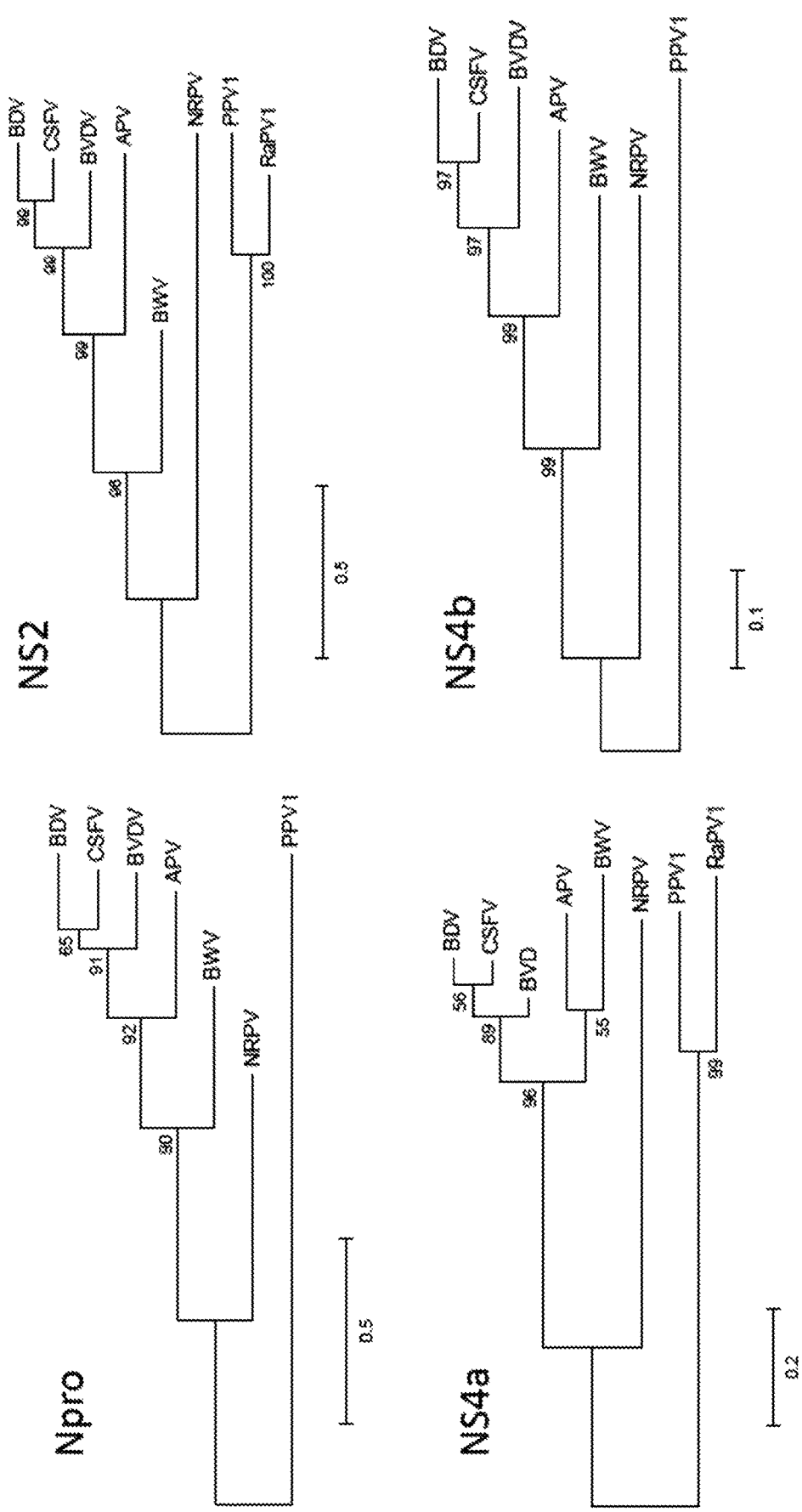
FIG. 1A shows phylogenetic trees of non-structural pestivirus proteins Npro, NS2, NS4a, and NS4b for various pestiviruses.

The present invention is concerned with identification of a novel virus designated herein as atypical porcine pestivirus ("APPV") (aka porcine pestivirus 1 (PPeV1) strain 000515). The virus and associated information is useful in diagnostic assays to detect porcine pestivirus, and vaccines to induce a protective immune response against porcine pestivirus infection.

The pestivirus genome generally consists of a single positive strand RNA approximately 12 kb in length which encodes a polyprotein approximately of 3,900 amino acids flanked by untranslated regions ~400 bp in length. The polyprotein is co- and post-translationally cleaved by a combination of cellular and viral-encoded proteases to generate 11-12 proteins. Genomic organization is conserved with protein order: Npro-C-Erns-E1-E2-p7-NS2/3-NS4A-NS4B-NS5A-NS5B. The pestivirus virion contains three structural glycoproteins: Erns, E1, and E2. Erns is a pestivirus envelope glycoprotein that is unique to pestiviruses.

Sequence information for the novel APPV isolate is available under Genbank accession no. KR011347.1, incorporated by reference herein. Molecular epidemiology and serology suggest that this virus is common in U.S. swine. The mRNA complementary (cDNA) coding sequence of the novel APPV isolate viral genome comprises (consists of) SEQ ID NO:1, and encodes for a polyprotein according to SEQ ID NO:2. The viral cDNA template can be used to synthesize mRNAs, which are then translated into viral proteins. In one or more embodiments, the APPV isolate comprises a gene (SEQ ID NO:3) encoding for an Erns protein. In one or more embodiments, the APPV isolate is one presenting an Erns epitope according to SEQ ID NO:4, or an epitope having at least 95% sequence identity to SEQ ID NO:4.

The APPV isolate can be used to prepare vaccines to induce a protective immune response against porcine pestivirus infection in a pig. The APPV isolate can be used as a live, attenuated (whole) virus vaccine. Various protocols for attenuating viruses are known in the art, including passaging of the virus in cell culture or in an unnatural host animal (e.g., mouse, chick embryos, etc.). The APPV isolate can also be used as an inactivated (non-replicating) whole virus vaccine. Such viruses can be prepared by heat or chemical treatment to inactivate the replicative function of the virus. Genetic modifications may also be made to yield attenuation or inactivation. For example, mutations in the catalytic active sites for the Erns protein can lead to virus attenuation (e.g., a virus that can replicate, but not infect). Synthetically generated viral constructs can also be used in such vaccines, wherein the virus is synthetically generated from genome segments constructed directly using known sequences and chemical or enzymatic synthesis and assembly of the oligonucleotides. For example, the synthetic expression construct can drive expression in a eukaryotic cell of viral segments encoded therein. The expressed viral segment RNA can be translated into a viral protein that can be incorporated into a virion. Molecular techniques can be used to synthesize an infectious clone of the virus, and subsequently introduce targeted mutations to knock down the function of virulent gene(s) to generated attenuated clones as well.

Sequence fragments may also be used so long as they are "functional fragments" meaning that they nonetheless encode a functional protein for the virus from which the sequence was derived. Vaccines can also be made using "derivatives" of the APPV isolate, which as used herein, refers to recombinant viral particles and chimeras including the APPV isolate or a functional fragment thereof. Vaccines can also be made with functional fragments of the APPV isolate, including subunits, purified antigens, surface proteins, and recombinant or synthetically generated forms thereof. Such viral fragments are "functional" so long as they encode for a functional antigenic protein of the APPV isolate that will provoke an immune response in the subject animal. Examples include the Erns protein, E2 protein, or NS3 protein of the APPV isolate. As such, the vaccines can include recombinant proteins or vectors that express APPV E2 or Erns recombinant proteins from APPV as vaccines. In some embodiments, such functional fragments can be coupled to a carrier protein or adjuvant for delivery. Similarly, functional fragments from APPV can be used in chimeric or recombinant viral particles to generate an immune response against APPV. Examples include recombinant or chimeric pestiviruses created via reverse genetics and pestivirus backbones other than APPV (e.g., BVD backbone with BVD E2 or Erns gene replaced with E2 or Erns from APPV).

As used herein, the term "vaccine" refers to an immunogenic composition capable of provoking an immune response against a disease or condition in the subject (e.g., swine) to which it has been administered. Compositions according to the embodiments disclosed herein are useful in treating viral infection from pestivirus in a subject (e.g., swine) and/or preventing or reducing clinical symptoms of infection. Such clinical symptoms are the manifestation of the neurological disease caused by the pestivirus and include tremors, increased respiration rate, lack of coordination (e.g., unbalanced walking, inability to stand-up), and/or inability to swallow or control mouth movements. Thus, embodiments described herein have therapeutic and/or prophylactic uses, and in particular can be used for prophylactic treatment of a viral infection. In general, the compositions are administered prophylactically, that is, before the subject demonstrates detectable clinical signs of an infection, such that the subject develops an adaptive immune response to infection by the virus. As such, the methods are useful for preventing the development of observable clinical symptoms from viral infection, and/or reducing the incidence or severity of clinical symptoms, and/or effects of the infection, and/or reducing the duration of the infection/symptoms/effects, and/or reducing the amount and/or duration viral shedding/viremia (e.g., excretion or expulsion of the virus or viral particles from an infected subject), as compared with unvaccinated control animals. Thus, the composition may only partially prevent and/or lessen the extent of morbidity due to the viral infection (i.e., reduce the severity of the symptoms and/or effects of the infection, and/or reduce the duration of the infection/symptoms/effects), as compared with unvaccinated control animals. Yet, the composition is still considered is still considered to treat or "prevent" the target infection or disease, even though it is not 100% effective. Another advantageous aspect of the invention is that protective immunity may be transmitted from vaccinated subjects to the offspring.

The vaccines comprise the APPV isolate described herein, derivative thereof, or functional fragment thereof, dispersed in a pharmaceutically-acceptable carrier. For ease of reference, the term "APPV antigenic agents" will be used to refer collectively to the APPV isolates (whole virus), derivatives thereof, or functional fragments thereof. The term carrier is used herein to refer to diluents, excipients, vehicles, and the like, in which the APPV antigenic agents may be dispersed for administration. Suitable carriers will be pharmaceutically acceptable. As used herein, the term "pharmaceutically acceptable" means not biologically or otherwise undesirable, in that it can be administered to a subject without excessive toxicity, irritation, or allergic response, and does not cause unacceptable biological effects or interact in a deleterious manner with any of the other components of the composition in which it is contained. A pharmaceutically-acceptable carrier would naturally be selected to minimize any degradation of the APPV antigenic agents or other ingredients and to minimize any adverse side effects in the subject, as would be well known to one of skill in the art. Pharmaceutically-acceptable ingredients include those acceptable for veterinary use, and will depend on the route of administration. For example, compositions suitable for administration via injection are typically solutions in sterile isotonic aqueous buffer. Exemplary carriers include aqueous solutions such as normal (n.) saline (~0.9% NaCl), phosphate buffered saline (PBS), sterile water/distilled autoclaved water (DAW), aqueous dextrose solutions, aqueous glycerol solutions, ethanol, normal allantoic fluid, various oil-in-water or water-in-oil emulsions, as well as dimethyl sulfoxide (DMSO) or other acceptable vehicles, and the like.

The vaccine can comprise a therapeutically effective amount of APPV antigenic agents dispersed in the carrier. As used herein, a "therapeutically effective" amount refers to the amount that will elicit the biological or medical response of a tissue, system, or subject that is being sought by a researcher or clinician, and in particular elicit some desired protective effect as against the viral infection by priming or stimulating an immune response specific to the APPV isolate. One of skill in the art recognizes that an amount may be considered therapeutically "effective" even if the condition is not totally eradicated or prevented, but it or its symptoms and/or effects are improved or alleviated partially in the subject. In some embodiments, the composition will comprise from about 5% to about 95% by weight of APPV antigenic agents described herein, and preferably from about 30% to about 90% by weight of APPV antigenic agents, based upon the total weight of the composition taken as 100% by weight. In some embodiments, combinations of more than one type of the described APPV antigenic agents can be included in the composition, in which case the total levels of all such viral particles will preferably fall within the ranges described above.

Other ingredients may be included in the composition, such as adjuvants, other active agents, preservatives, buffering agents, salts, other pharmaceutically-acceptable ingredients, including residual amounts of ingredients used in vaccine manufacturing. The term "adjuvant" is used herein to refer to substances that have immunopotentiating effects and are added to or co-formulated in the vaccine composition in order to enhance, elicit, and/or modulate the innate, humoral, and/or cell-mediated immune response against the vaccine components. Suitable adjuvants include: aluminum salts, such as aluminum hydroxide, aluminum phosphate, alum (potassium aluminum sulfate), or mixed aluminum salts, peptides, oil or hydrocarbon emulsions, or any other adjuvant deemed suitable for animal use. Other active agents that could be included in the composition include other antiviral compounds or any immunogenic active components (e.g., antigens) such as those that resemble a disease-causing microorganism or infectious agent other than the APPV, and/or are made from weakened or killed forms of the same, its toxins, subunits, particles, and/or one of its surface proteins, such that it provokes an immune response to that microorganism or infectious agent. In addition to live, modified, or attenuated vaccine components, active agents using synthetic peptides, carbohydrates, or antigens can also be used. Antibiotics can also be used as part of vaccine production and may be present in small amounts in the vaccine, such as neomycin, polymyxin B, streptomycin and gentamicin. In some embodiments, the vaccine composition is substantially free of any other active (immunogenic) agents, other than the APPV antigenic agents and optional adjuvant, dispersed in the carrier.

In use, the vaccine composition is administered to a subject. In general, the subject would be an animal susceptible to pestivirus. In some embodiments, the immunogenic composition is administered to a pregnant animal to induce immunity indirectly in her offspring through passive transfer of maternal antibodies. In some embodiments, the invention is concerned with methods of conferring immunity to piglets against pestivirus by administering to pregnant sows an effective amount of APPV antigenic agents, wherein the resulting piglet(s) have a reduced morbidity and/or mortality as compared to piglets born by unvaccinated sows.

Various routes of administration can be used depending upon the particular carrier and other ingredients used. For example, the vaccine can be injected intramuscularly, subcutaneously, intradermally, or intravenously using a needle and syringe, or a needleless injection device. The vaccine can also be administered mucosally, such as intranasal administration. For intranasal administration, the vaccine composition is usually administered through the nasal passage as drops, large particle aerosol (greater than about 10 microns), or spray into the upper respiratory tract. Oral administration may encompass, for example, adding the compositions to the feed or drink of the animals. While stimulation of a protective immune response with a single dose is preferred, additional dosages can be administered, by the same or different route, to achieve the desired prophylactic effect. The vaccine can also be administered using a prime and boost regime if deemed necessary. In some embodiments, the methods described herein are useful for reducing the occurrence or incidence of pestivirus and/or reducing the effects of pestivirus infection, as described above.

Regardless, administration of the APPV antigenic agents elicits an immune response in the animal (or offspring, if applicable). Such an "immune response" includes, for example, the production or activation of antibodies, B cells and/or the various T cells, directed specifically to an antigen or antigenic component of the APPV isolate (e.g., E1, E2, Erns, NS3, etc.). The immune response will be demonstrated by a lack of observable clinical symptoms, or reduction of clinical symptoms normally displayed by an infected animal, faster recovery times from infection, reduced duration or amount of viral shedding, and the like. Accordingly, vaccinated animals will display resistance to new infection (or observable signs of infection) or reduced severity of infection, as compared to unvaccinated animals. The invention is particularly concerned with pigs, in all stages of development, including newborn, embryonic, and fetal stages.

"Reducing" the incidence, severity, and/or duration of clinical symptoms and/or viral shedding, means reducing the number of infected animals in a group, reducing or eliminating the number of animals exhibiting clinical signs of infection, or reducing the severity of any clinical signs that are present in the animals, in comparison to wild-type infection in unvaccinated animals. Preferably, these are reduced in animals receiving the APPV antigenic agents of the present invention by at least 10% in comparison to animals not receiving the vaccination which may become infected. More preferably, clinical symptoms of infection are reduced in animals receiving the vaccination by at least 20%, more preferably by at least 30%, even more preferably by at least 40%, and even more preferably by at least 50%.

In some embodiments, the vaccine can be provided in unit dosage form in a suitable container. The term "unit dosage form" refers to a physically discrete unit suitable as a unitary dosage for animal use. Each unit dosage form may contain a predetermined amount of the vaccine (and/or other active agents) in the carrier calculated to produce the desired effect. In other embodiments, the vaccine can be provided separate from the carrier (e.g., in its own vial, ampule, sachet, or other suitable container) for on-site mixing before administration to a subject. A kit comprising the vaccine is also disclosed herein. The kit further comprises instructions for administering the vaccine to a subject. The APPV antigenic agents can be provided as part of a dosage unit, already dispersed in a pharmaceutically-acceptable carrier, or the APPV antigenic agents can be provided separately from the carrier. The kit can further comprise instructions for preparing the virus for administration to a subject, including for example, instructions for dispersing the APPV antigenic agents in a suitable carrier.

In one or more embodiments, vaccination against pestivirus can be combined with other vaccinations within the framework of vaccination programs, in the form of immunization or vaccination kits or methods, or in the form of multivalent immunogenic compositions and multivalent vaccines, i.e. comprising or consisting essentially of at least one vaccine component against APPV and at least one vaccine component against at least one other pathogenic agent.

The methods can be also applied for clinical research and/or study. A diagnostic method for pestivirus infection in a subject is also disclosed. The method includes contacting a biological sample from a subject with a monoclonal antibody against the APPV isolate or a fragment thereof. The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. Antibodies can be naked or conjugated to other molecules such as toxins, radioisotopes, etc. A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals. The term "specifically binds" refers to the antibody reacting or associated more frequently, more rapidly, with greater duration, with greater affinity, or with some combination of the above to an epitope or protein than with alternative substances, including unrelated proteins.

In one or more embodiments, the monoclonal antibody is one that specifically binds to the a surface protein (e.g., E1, E2, Erns) of the described APPV isolate, if present, in the sample. In one or more embodiments, the antibody binds to an epitope having SEQ ID NO:4, or at least 95% sequence identity to SEQ ID NO:4. In one or more embodiments, functional antibody fragments are contemplated as long as they nonetheless bind specifically to the target epitope. This antibody-antigen binding can then be detected using various techniques. For example, in one or more embodiments, the antibody (or fragment) can be conjugated with a detectable label. Exemplary labels include fluorophores, biotin, radioisotopes, enzymes, and the like. Various techniques are available for detecting the antibody-antigen binding, depending upon the label used. Non-limiting examples include enzyme-linked immunosorbent assay (ELISA), immunofluorescence, immunohistochemistry, immunochromatography, flow cytometry, immunoprecipitation, and Western blot.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

Characterization of New Porcine Pestivirus

In this study, a novel porcine pestivirus isolate designated as PPeV1 or alternatively as APPV ("atypical porcine pestivirus") was identified and characterized.

Materials and Methods:

Ethics Statement. Porcine serum samples used in this study were submitted to Kansas State Veterinary Diagnostic Laboratory (KSVDL), Iowa State University Veterinary Diagnostic Laboratory or the South Dakota State University Animal Disease Research and Diagnostic Laboratory for routine diagnostic testing. The samples were obtained from naturally infected animals in the field by licensed veterinarians as a part of normal veterinary care and diagnostic investigations.

Collection of Samples. Metagenomic sequencing was performed on 182 swine serum samples that were quantitative real time reverse transcription PCR (qRT-PCR) positive for PRRSV. The serum samples were submitted to KSVDL, Iowa State University Veterinary Diagnostic Laboratory or the South Dakota State University Animal Disease Research and Diagnostic Laboratory for PRRSV qRT-PCR. The samples originated from thirteen states (Iowa [n=35], Minnesota [n=39], South Dakota [n=2], Texas [n=9], North Carolina [n=18], Nebraska [n=14], Kansas [n=22], Oklahoma [n=1], Illinois [n=2], Indiana [n=1], Missouri [n=1], Arizona [n=2], and Colorado [n=4]), Mexico (n=4) and unknown (n=28). A collection of 292 PRRSV-negative swine serum samples submitted to KSVDL for diagnostic testing were screened for the presence of porcine pestivirus 1 (PPeV1) using a qRT-PCR assay targeting the E2 region of the genome.

Metagenomic Sequencing. Sample preparation for metagenomic sequencing was performed similar to previously described (Hause B M, Collin E A, Anderson J, Hesse R A, Anderson G. 2015. Bovine rhinitis viruses are common in U.S. cattle with bovine respiratory disease. PLOS One 10:e0121998). Serum samples were treated with a cocktail of nucleases to degrade host or unprotected environmental nucleic acids at 37° C. for 90 minutes. Viral nucleic acids were isolated using the MinElute Virus spin filter kit (Qiagen, Valencia, Calif.) according to the manufacturer's instructions. Reverse transcription was performed using primers consisting of a known 20 nt sequence followed by a random hexamer at the 3' end using a Superscript III reverse transcription kit (Life Technologies, Grand Island, N.Y.). Second strand synthesis was performed using Sequenase 2.0 (Affymetrix, Santa Clara, Calif.). Double stranded cDNA was purified using a Qiagen Minelute PCR spin column and subsequently amplified using primers identical to the ones used for reverse transcription but lacking the random hexamer. Amplicons were purified using a Qiagen Minelute PCR spin column and quantified using a Qubit fluorimeter (Life Technologies, Grand Island, N.Y.). Sequencing libraries were prepared using the Nextera XT library preparation kit (Illumina, San Diego, Calif.) according to manufacturer's instructions. Pooled barcoded libraries were sequenced on an Illumina MiSeq instrument using paired 150 bp reads.

Reads from each sequencing library were parsed into individual folders based on barcoded sequences. Reads were imported into the CLC Genomics software package (Qiagen, Valencia, Calif.). Reads were mapped to the host genome (*Sus scrofa*) and unmapped reads were collected. De novo assembly was performed on unmapped reads and assembled contigs were analyzed by BLASTN. Sequences were aligned using ClustalW and phylogenetic analyses were performed by using Mega6.06 software using the Maximum Likelihood algorithm with tree topology verified by performing 1000 bootstrap replicates.

Molecular Screening for Porcine Pestivirus 1

A 5'-nuclease reverse transcription PCR assay was designed to detect PPeV1 targeting the E2 region of the genome: probe, 5'-FAM-TTT AGA CAC GAC CCC TCA GCC C-Iowa Black-3' (SEQ ID NO:5); Forward: 5'-CCA CTT GCC CAT TAT AGA CCG-3'(SEQ ID NO:6); Reverse: 5'-TTA TGG TGC CTG TTA CTG TCT G-3'(SEQ ID NO:7). A second 5'-nuclease reverse transcription PCR assay targeting the Erns region of the genome was also designed: probe, 5'-FAM-ACC TCG TCT CTG GCC TGT CTC A-Iowa Black-3'(SEQ ID NO:8); Forward, 5'-AGT GTG CTG TCA TCT GTC G-3'(SEQ ID NO:9); Reverse, 5'-CTT CCT TAC ACC CTG TCA GTG-3'(SEQ ID NO:10). Viral RNA was extracted using the MagMAX-96 viral RNA isolation kit (Life Technologies, Grand Island, N.Y.) according to the manufacturer's instructions. Quantitative real time reverse transcription PCR (qRT-PCR) was performed using Qiagen Quantitect RT-PCR with E2 or Erns primers and probe as follows: 50° C., 30 minutes; 95° C., 15 minutes; followed by 40 cycles of 94° C. for 15 seconds and 60° C. for 60 seconds. The PCR assay specificity was confirmed using PPeV1 positive samples as determined by metagenomic sequencing as well as with cultures of common swine respiratory viruses, influenza A virus and PRRSV and two different pestivirus species, BVDV-1 and BVDV-2.

Viral Isolation

Virus isolation was attempted on various primate, bovine, swine and canine cell lines. They included primate MARC-145, Vero, Vero 76, and human rectal tumor cells (HCT-8). Bovine cells included bovine turbinates (BT) and Madin-Darby bovine kidney (MDBK) cells. Swine cell lines included swine testicle cells (ST) and porcine kidney cells (PK-15). Virus isolation was also attempted on Madin-Darby canine kidney cells (MDCK). All cell lines were maintained in minimal essential media (MEM) supplemented with L-glutamine and 5% fetal bovine sera. Cell culture fluids were removed from the 12-well plates (>80% confluency) and 25-100 uL of sample (depending on available sample volume) was inoculated into 1 mL of viral replacement media, which consisted of MEM and penicillin-streptomycin solution. Plates were incubated 5 days before being frozen, thawed, and passaged as above to fresh monolayers. Cells were observed daily for cytopathic effects and PPeV1 growth was monitored by qRT-PCR.

Serology

The PPeV1 Erns regions (fragment A: 20-120aa; fragment B: 45-150aa) were amplified from genomic RNA by RT-PCR and the PCR products were cloned into the pET-28a (+) vector (Novagen, Madison, Wis.), which contains a His-tag at its N-terminus for facilitating downstream protein purification. The resulting plasmids, pET28-Erns-A and pET28-Erns-B, were transformed into *E. coli* BL21 (DE3) cells. Transformed cells were cultured in 2× yeast extract tryptone (YT) medium and the protein expression was induced using isopropyl β-d-1-thiogalactopyranoside (IPTG). The recombinant proteins were extracted using B-PER reagent (Pierce, Rockford, Ill.), and further purified by the Ni-NTA agarose (Qiagen, Valencia, Calif.) following the manufacturer's instruction. The purified recombinant proteins Erns-A and Erns-B were suspended in 1× phosphate buffered saline (PBS), aliquoted and frozen at −80° C.

Erns-A and Erns-B purity were assessed by polyacrylamide gel electrophoresis using denaturing conditions and Western blotting using an antibody directed against the His-tag. The protein samples were separated by sodium dodecyl sulfate-polyacrylamide gel electrophoresis (SDS-PAGE). Protein bands were visualized by staining with Coomassie brilliant blue G-250 (Bio-Rad, Hercules, Calif.). To confirm the expression of target proteins, Western blotting assay was performed. The proteins in the SDS-PAGE gel were electro-transferred onto a nitrocellulose membrane (Whatman, Piscataway, N.J.). The membrane was then incubated for 2 hour at room temperature with anti-Histidine monoclonal antibody (mAb; Novagen, Madison, Wis.). After a 3× wash with phosphate buffered saline containing 0.05% Tween 20 (PBST), IRDye 800CW-conjugated goat anti-mouse antibody (LI-COR Biosciences, Lincoln, Nebr.) was added and the membrane was incubated at room temperature for 2 h. The Image of the membrane was finally taken under the appropriate excitation wavelength using a digital imaging system (Odyssey infrared imaging system; LI-COR Biosciences).

ELISA assays were performed similar to previous studies on CSFV. Immulon 2HB plates were coated with 100 µL of 0.1 M sodium carbonate buffer (pH 9.6) containing 2 µg/mL of each recombinant Erns fragment at room temperature for 20 hours. The coating solution was removed and plates were frozen at −20° C. until use. Plates were thawed and washed with PBST before being blocked 1 hour at 37° C. with 100 µL/well Starting Block (Thermo Fisher Scientific, Waltham, Mass.). Plates were washed three times with PBST and then 100 µL of 1:100 diluted serum samples (diluted in PBST) were applied to single wells. Plates were incubated at 37° C. for 1 hour before being washed three times with PBST. Horse radish peroxidase-labeled goat anti-swine IgG was diluted 1:2,000 in PBST and 100 µL was added to each well and incubated at 37° C. for 1 hour. Plates were washed three times with PBST and developed with a commercial peroxidase colorimetric assay kit (ABTS ELISA HRP substrate, KPL, Gaithersburg, Md.) at room temperature for 10 minutes before the reaction was stopped with stop solution. The absorbance at 405 nm was measured with a plate reader. Mean optical density values per group were analyzed using ANOVA and Tukey-Kramer honest significant difference tests as implemented in ATP software (SAS, Cary, N.C.). Samples were analyzed concurrently on the same day.

Nucleotide Accession Numbers. The genome sequence of PPeV1 was submitted to GenBank under accession number KR011347, incorporated by reference herein.

Results

Identification of a novel porcine pestivirus. Metagenomic sequencing was performed on a sample that was qRT-PCR positive for PRRSV as part of a PRRSV metagenomic sequencing project. Following subtraction of reads mapping to the host Sus scrofa, reads were assembled de novo into 2,167 contigs and analyzed by BLASTN. The largest contig, 1,343 base pairs (bp), was most similar to CSFV (expectation value, $E=4.2\times10^{-11}$). Four additional contigs were identified which were most similar to pestiviruses ($E=2.73\times10^{-48}$ to BVD; $E=9.9\times10^{-8}$, $4.04\times10^{-87}$ and $1.50\times10^{-60}$ to Rhinolophus affininis pestivirus 1 [RaPV1]). Resequencing of the sequencing library coupled with PCR targeting gaps in the assembly resulted in an 11,276 bp contig encoding a predicted 3,635 amino acid (a.a.) polyprotein with an overall 68% identity to the partial polyprotein sequence of RaPV1 and approximately 40% identity to complete polyprotein amino acid sequences of BVDV, BDV and CSFV (Table 1).

TABLE 1

BLASTP analysis of the twelve putative mature proteins and the polyprotein of atypical porcine pestivirus (APPV)

| Region | Size (amino acids) | Best BLAST Hit (accession number) | Query Coverage (%) | E value | Identity (%) |
|---|---|---|---|---|---|
| Npro | 180 | none | none | none | none |
| C | 111 | BVDV (NP_776260) | 89 | $1e^{-5}$ | 37 |
| Erns | 210 | CSFV (AFE56244) | 97 | $2e^{-43}$ | 43 |
| E1 | 199 | BVDV (ACV83744) | 98 | $1e^{-27}$ | 32 |
| E2 | 241 | RaPV (AFK85014) | 100 | $4e^{-87}$ | 54 |
| P7 | 64 | RaPV (AFK85014) | 100 | $2e^{-19}$ | 67 |
| NS2 | 314 | RaPV (AFK85014) | 100 | $4e^{-125}$ | 60 |
| NS3 | 687 | RaPV (AFK85014) | 100 | 0 | 74 |
| NS4a | 67 | RaPV (AFK85014) | 100 | $1e^{-20}$ | 61 |
| NS4b | 339 | RaPV (AFK85014) | 76 | $4e^{-110}$ | 76 |
| NS5a | 472 | BDV (AHM88396) | 45 | $2e^{-6}$ | 26 |
| NS5b | 751 | CSFV (AAT85641) | 89 | 0 | 50 |
| Polyprotein | 3635 | RaPV (AFK85014) | 46 | 0 | 68 |

Notably, this polyprotein is greater than 250 residues smaller than other pestiviruses. The results suggest that this virus represents a novel member of the Pestivirus genus and was provisionally named porcine pestivirus 1 (PPeV1). Putative PPeV1 mature protein sequences were identified by alignment with reference pestivirus genomes and known cleavage sites as determined for CSFV strain Alfort.

Genome Characterization

Untranslated Regions

The 5'-untranslated region (UTR) determined encompassed 123 bp which is considerably shorter than those for other pestiviruses (~370-498 bp). Attempts to verify the termini sequences by random amplification of cDNA ends (RACE) failed, likely due to insufficient virus titer (Ct~30). BLASTN analysis of the 5'-UTR failed to identify any significant ($E<1\times10^{-5}$) hits. The 5'-UTR of the genome is the most highly conserved region of pestiviruses and is frequently the target for molecular detection and taxonomical classification. With the exception of the newly described NRPV, all pestiviruses share >70% nt identity in the 5'UTR. The PPeV1 5'-UTR has less than 20% nt identity to all known pestiviruses. Likewise, the 3'UTR failed to show any similarity to known sequences in Genbank. The 245 bp of sequence determined for the 3'UTR is consistent with the length of other pestivirus 3'UTR's (~200-500 bp) but further experimentation is needed to demonstrate its completeness.

Npro

The Npro protein is unique to the genus Pestivirus and is a non-structural autoprotease. Npro catalyzes self-cleavage from the polyprotein between Cys168 and Ser169. The predicted Npro protein of PPeV1 is 180 amino acids, slightly larger than the typical 168 amino acids of most pestiviruses with the exception of NRPV (273 a.a.), and contains a Cys180-Ser181 cleavage motif. The conserved Npro catalytic site consisting of Glu22, His49 and Cys69 were identified in PPeV1 at Glu 20, His69 and Cys89 by pairwise alignment with known pestiviruses. Despite conservation of the catalytic and cleavage sites, the Npro protein sequence had no significant similarity to any known proteins by BLASTP analysis.

Core

Pestiviruses encode a small, basic core protein (C) which possesses RNA chaperone activity and plays a role in RNA packaging into virions. At 113 a.a. in length, the C protein of PPeV1 is slightly larger than other pestivirus C proteins (97-102 a.a.) but has a predicted isoelectric point of 10.4, similar to other pestiviruses. The PPeV1 C protein has ~37% identity to those of BVDV, BDV, CSFV and BWV.

Envelope Proteins

Pestiviruses encode three envelope glycoproteins, E1, E2 and Erns. The Erns protein, found only in pestiviruses, is the only known viral structural protein with a ribonuclease T2 domain with uridinylate specificity. The ribonuclease T2 domain was identified in the PPeV1 Erns region of the genome from a.a. 319-373 using the National Center for Biotechnology Information (NCBI) Conserved Domain Database. The PPeV1 Erns length was slightly shorter than other pestiviruses (208 a.a. and 214-227 a.a., respectively) and has 39-42% identity to BVDV, BDV and CSFV.

E1 and E2 form heterodimers on the virus surface that are crucial for viral entry into cells. The E2 protein is also immunodominant and possesses neutralization epitopes and consequently is the pestivirus protein that exhibits the greatest amount of diversity. Both proteins displayed 29-33% identity to BVD and CSFV however E2 was 54% identical to the recently described RaPV1. It should be noted that only 5.1kb of the RaPV1 genome is known, encompassing the E2, P7, NS2, NS3 and NS4a regions of the genome. Interestingly, while the length of the E1 proteins were similar for all pestiviruses (195-215 a.a.), the E2 proteins for PPeV1 and RaPV1 were significantly shorter (241 and 244 a.a., respectively) than all other pestiviruses (373-378 a.a.). The deletion accounting for the smaller size of the PPeV1 E2 protein was located at the N-terminus.

Nonstructural Proteins

NS2 is a cysteine autoprotease responsible for cleavage of NS2 from NS3. The length of PPeV1 NSP2 (315 a.a.) was similar to that of RaPV1 NSP2 (318 a.a.) and significantly shorter than NSP2 from other pestiviruses (455-543 a.a.). A search of PPeV1 NSP2 failed to identify conserved protease domains. BLASTP analysis of the PPeV1 NSP2 found significant similarity only to RaPV1 NSP2 (60% identity). The active site of NSP2 has a His1447 and Cys1512 and is thought to include a glutamate residue between 1447-1512. Multi-sequence alignment identified a conserved His1237 and Glu1253 however the conserved cysteine residue of the catalytic triad could not be identified. One candidate cysteine residue at position 1280 was identified. NS3 is a chymotrypsin-like serine protease catalyzing both cis and trans-cleavage. The PPeV1 NS3 protein shared relatively high identity to the NS3 of RaPV1 (74% identity) and 45-47% identity to other pestiviruses. Conserved domains identified include a DEAD-like helicase from 1547-1672 and a pestivirus peptidase S31 domain from 1320-1530. NS4a, NS4b, NS5a and NS5b are all involved with pestivirus replication. NS4a and NS4b were 61% and 76% identical to RaPV1 NS4a and NS4b, respectively, and 37-43% identical to BDV, BVDV and CSFV. NS5a shared only 24-28% identity to other pestiviruses. NS5b codes for the RNA dependent RNA polymerase (RdRp) and is one of the most conserved pestivirus proteins. NS5b from PPeV1 was 50% identical to CSFV and a RdRp domain was identified from 3153-3438. The P7 protein is a small hydrophobic peptide 61-72 a.a. in length that functions as a viroporin that is essential for virus production in vitro and virulence in vivo. The P7 of PPeV1 was 67% identical to the P7 of RaPV1 and lacked significant similarity to any other proteins in GenBank.

Phylogenetic Analysis

Figure 1B:
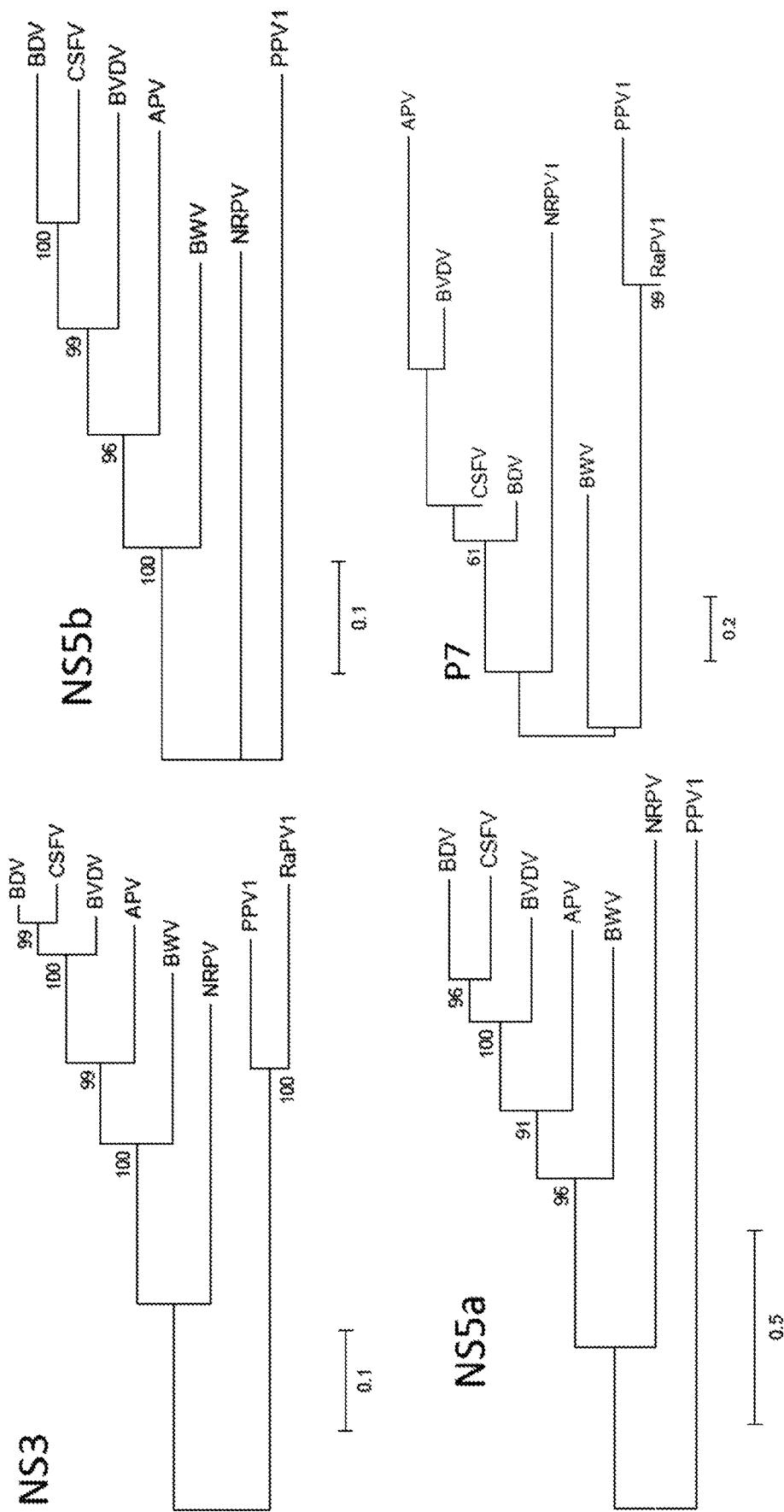
FIG. 1B shows phylogenetic trees of non-structural pestivirus proteins NS3, NS5a, NS5b, and P7 for various pestiviruses.
Figure 1C:
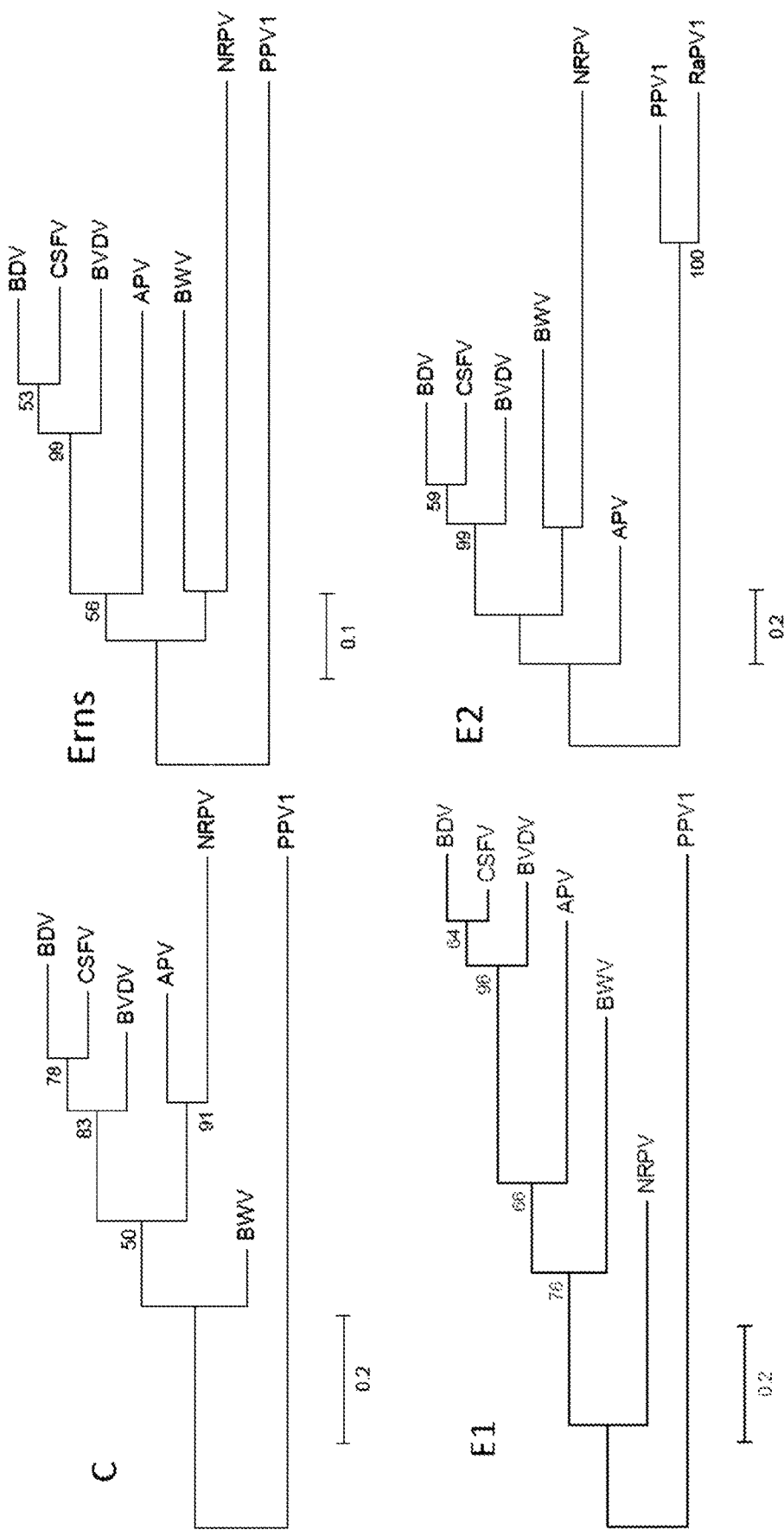
FIG. 1C shows phylogenetic trees of structural pestivirus proteins C, Erns, E1, and E2 for various pestiviruses.

Phylogenetic trees constructed using amino acid sequences of predicted pestivirus nonstructural and structural proteins are shown in FIGS. 1A-1C. Maximum-likelihood analysis in combination with 500 bootstrap replicates as implemented in MEGA 6.06 was used to derive trees based on the predicted protein sequences. A scale representing the number of amino acid changes is shown in each Figure. Abbreviations are as follows with GenBank accession numbers in parentheses: BDV, border disease virus (NC003679); RPV, reindeer pestivirus (AAF02524); CSFV, classical swine fever virus (NC002657); GPV, giraffe pestivirus (NP620053); BVDV, bovine viral diarrhea virus (NC001461); Hobi, HoBi virus (BA004453); APV, antelope pestivirus (NC024018); Bungo, Bungowannah virus (NC023176); NRPV, Norway rat pestivirus (NC025677); RaPV, *Rhinolophus affinis* pestivirus 1 (JQ814854); PPV1, atypical porcine pestivirus (KR011347). APPV/PPeV1 and RaPV1 formed a distinct cluster for all proteins where RaPV1 sequence is available with the exception of P7. The PPV1/RaPV1 cluster represented a highly divergent lineage of pestiviruses that evolved from an ancestral pestivirus.

Virus Isolation

Virus isolation was attempted on MARC-145, Vero, Vero 76, HCT-8, BT, MDBK, ST, PK15 and MDCK cell lines. No CPE was evident in any cell line. Viral titers were monitored by the E2 RT-PCR. Following two passages on cells all samples were qRT-PCR negative.

Molecular Epidemiology

As part of a project investigating PRRSV genetic diversity using metagenomic sequencing of swine serum samples, a total of 182 samples were sequenced using viral metagenomic methodology. Templated assembly was performed on these 182 samples using the PPeV1 genome. Reads mapping to the PPeV1 genome were identified in five samples. To confirm these results, two Taqman qRT-PCR assays were designed, targeting either the E2 or Erns region of the genome. The original sample, #146, was positive for both assays with cycle threshold (Ct) values of 25.1 and 30.5 (1:10 dilution of RNA), respectively. Sample #208 was only tested on the E2 qRT-PCR assay due to insufficient sample and was positive with Ct=19.3. Samples #51 and #98 were positive on both assays with Ct=33.2 and 36.2 for the E2 assay and Ct=33.9 and 34.1 for the Erns assay, respectively. Sample #28 was negative on the E2 assay but was positive with a Ct=32.3 for the Erns assay. All samples were positive for PRRSV as determined using a commercial PRRSV qRT-PCR assay and metagenomic sequencing. We also screened a collection of 292 PRRSV qRT-PCR negative serum samples. These samples were submitted to KSVDL for unrelated diagnostic testing. Using the E2 qRT-PCR assay all samples were negative.

For samples #208 and #28, there was sufficient read coverage for the E2 region of the genome to assemble complete and partial E2 sequences, respectively. The E2 sequence for #208 was identical to #146. For sample #28, a 197 a.a. portion of the E2 protein was assembled that was 88% identical to sample #146. The five positive samples were collected in 2014 from Nebraska, Arizona, North Carolina, Minnesota and Kansas, suggesting widespread distribution of PPeV1 in the U.S. swine herd. The finding of only 88% a.a. identity for the partial E2 sequence of sample #28 also suggests significant genetic diversity is present in PPeV1 and is likely the reason for the failure of the E2 assay to detect sample #28.

Serology

Figure 2A:
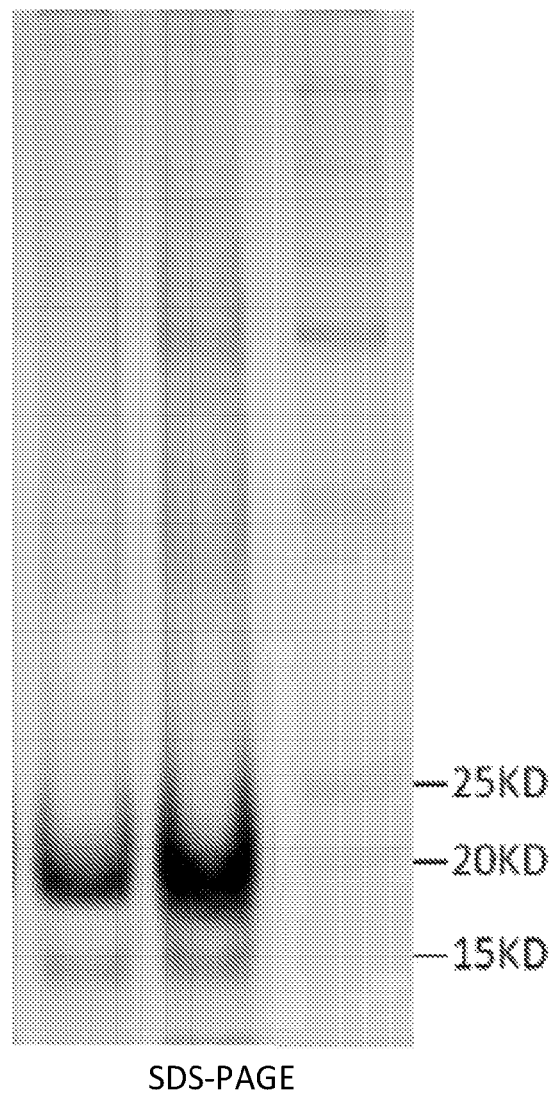
FIG. 2A shows SDS-PAGE analysis of protein purity for the APPV Erns fragments (Erns-A: 20-120aa; Erns-B: 45-150aa) expressed in *E. coli* N-terminal 6×His fusion proteins and purified using affinity chromatography.
Figure 2B:
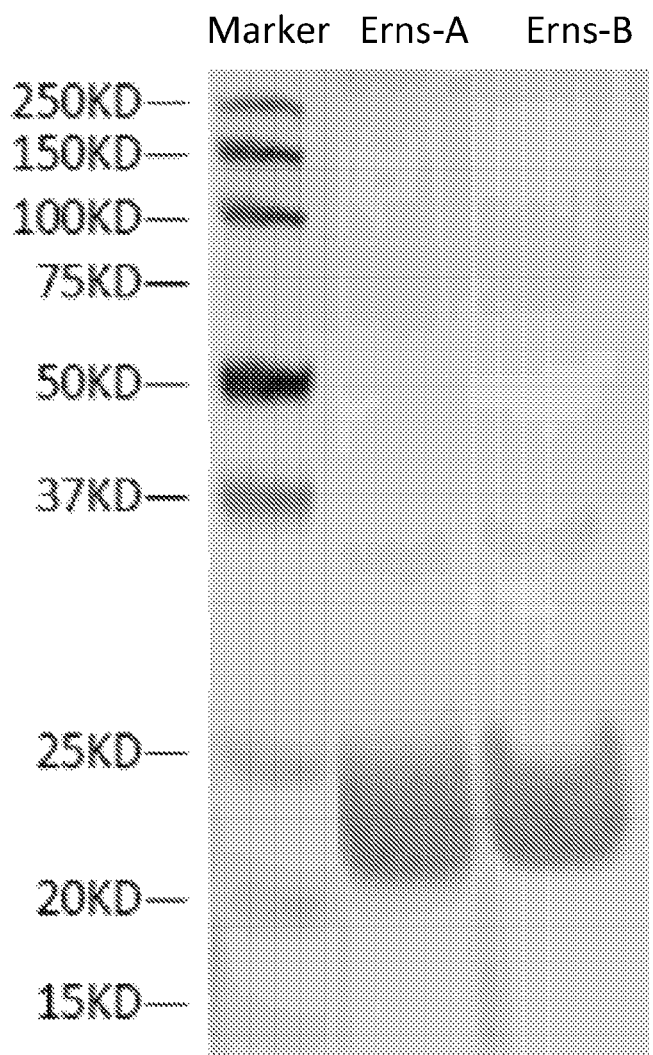
FIG. 2B shows Western blot analysis using a monoclonal anti-6×His antibody of protein purity for the APPV Erns fragments (Erns-A: 20-120aa; Erns-B: 45-150aa) expressed in *E. coli* N-terminal 6×His fusion proteins and purified using affinity chromatography.

The purity of the two Erns fragments were assessed by protein electrophoresis and Western blotting (FIG. 2). Large bands approximately 20 kDa were observed (as expected) for both fragments and only very faint additional bands were evident. A collection of 78 PRRSV qRT-PCR positive serum samples collected from multiple states, 90 PRRSV antibody-positive samples collected from a single site, 30 and 48 PRRSV antibody-negative serum samples collected from individuals at two production sites and 15 specific pathogen free pigs were assayed on the PPeV1 Erns ELISA. Mean group optical density (O.D.) values ranged from 0.48-1.25 (Table 2).

TABLE 2

Detection of antibodies cross reactive to atypical porcine pestivirus Erns peptides produced in E. coli. PRRSV qRT-PCR positive samples were collected from multiple sites representing at least seven states. Sera in other groups were collected from a single site.

| Serum Samples | $n^1$ | Mean O.D.[2] | Standard Deviation (O.D) | Positive Samples[3] (%) |
|---|---|---|---|---|
| PRRSV qRT-PCR Positive | 78 | $1.25^A$ | 0.33 | 73/78 (94) |
| Farm 1 | 90 | $1.06^B$ | 0.15 | 90/90 (100) |
| Farm 2 | 48 | $0.96^C$ | 0.12 | 46/48 (96) |
| Farm 3 | 30 | $0.57^D$ | 0.06 | 0/30 (0) |
| Specific Pathogen Free Pigs | 15 | $0.48^D$ | 0.08 | 0/15 (0) |

[1]Number of serum samples
[2]Optical Density (O.D.). Groups not connected by the same letter are significantly different (P < 0.05)
[3]A cutoff of O.D. > 0.72 was used to determine positivity All group mean O.D. values were significantly different from one another with the exception of the PRRSV antibody negative farm 2 and the negative control SPF pig group (P<0.05). The value of the mean negative control plus three standard deviations has been used to determine the negative cutoff for ELISA assays without well-defined positive controls. Applying this formula to the negative controls yielded a cutoff value O.D.>0.72. For the PRRSV qRT-PCR sample set, 73/78 (94%) of samples are positive. For samples from a single farm, 90/90 (100%) pigs from the PRRSV antibody positive and 46/48 (96%) and 0/30 (0%) of the pigs in the two PRRSV antibody-negative farms were positive.

Discussion

Pestiviruses are economically one of the most significant genera of viruses affecting livestock. Prior to eradication from the U.S. in 1978, classical swine fever plagued swine production since its identification in the 1830's. Currently, CSFV is widespread in Central and South America, the Caribbean, Asia and Eastern Europe. Likewise, BVDV, first reported in the 1940's, is generally regarded as one of the most economically significant diseases affecting cattle with near worldwide distribution. The other major pestivirus, BDV, mainly affects sheep and is also widely distributed. CSFV, BVDV and BDV are closely related and interspecies transmission and infection have been well documented. With the exception of descriptions of pestivirus genotypic variants in other species such as pronghorn antelope pestivirus and giraffe pestivirus, our knowledge of the breadth of pestivirus diversity has been limited until recent times. An outbreak of stillbirths and sudden deaths in swine in Australia, 2003, was attributed to a novel, divergent pestivirus, BWV, which was proposed to represent a new species. More recently with the advent of next generation sequencing technology, yet more divergent pestiviruses were identified in rats and bats (NRPV and RaPV1, respectively), expanding the diversity and host range of pestiviruses. While little is known on the pathogenic potential of the rat and bat pestiviruses, we have expanded our knowledge of the ecology of pestiviruses. In this study we report the identification and characterization of the complete polyprotein sequence of the most divergent pestivirus described to date and importantly demonstrate its widespread circulation in the U.S. swine herd.

PPeV1 was identified in five swine serum samples that were part of a set of 182 (2.7%) that were analyzed by metagenomic sequencing aimed at elucidating complete PRRSV genomes directly from clinical samples. While clinical histories are unknown, all serum samples were submitted to Veterinary Diagnostic Laboratories for PRRSV qRT-PCR. Unexpectedly, PPeV1 qRT-PCR assays failed to detect PPeV1 in a collection of 292 PRRS negative sera. These results suggest that PPeV1 is more common in pigs infected with PRRSV. PRRSV establishes persistent infections in pigs and results in immunosuppression. Host immunosuppression and persistent infections are also hallmarks of pestivirus infections and similar viral strategies are employed by PRRSV and pestiviruses to evade host immunity including induction of tolerance by in utero infection, innate immunity antagonism and a high mutation rate. Similarly, recent work demonstrated an association between PRRSV infection and reverse zoonotic influenza B virus infection in pigs. Further research is needed to determine if there is synergy between PPeV1 and PRRSV infections.

We were unable to isolate PPeV1 on any cell line assayed despite attempting virus isolation on the qRT-PCR positive samples, preventing us from performing serum neutralization or indirect immunofluorescence assays to gauge seroprevalence. To expand upon the results from our molecular testing, we expressed two Erns peptides in E. coli and assayed PRRSV qRT-PCR positive sera collected from at least seven states as well as sera from one PRRSV antibody positive and two PRRSV antibody negative farms. In contrast to our molecular assays, results suggest that PPeV1 infections can occur without PRRSV co-infections. Greater than 90% of serum samples collected from PRRSV qRT-PCR diagnostic sample submissions and from the PRRSV antibody positive and one PRRSV antibody negative farm were positive for antibodies that cross react with PPeV1 Erns. All pigs in the second PRRSV antibody negative farm were negative on the ELISA. This result suggests that the assay is specifically measuring antibodies cross reactivity with Erns and not measuring non-specific interactions. Not unexpectedly, a wide range of O.D. values were observed for the diverse collection of PRRSV qRT-PCR positive serum while much lower variability was observed in samples collected from a single site. These results suggest that PPeV1 infections are common in pigs and that the association with PRRSV co-infection suggested by molecular assay results is unclear. Similar high seroprevalence rates have been observed in cattle to influenza D virus with similar low qRT-PCR positivity rates. These serological results require substantiation by additional assays including control samples with known serological status.

The Npro protein is found only in the genus Pestivirus. Besides autocatalytic activity, Npro subverts cellular antiviral responses through degradation of IRF3 to prevent apoptosis and interferon production and also plays a role in viral RNA translation. While the protease catalytic residues and autoprotease cleavage sites were conserved, overall the Npro protein had no significant similarity to known proteins. Further experimentation is required to determine if the PPeV1 Npro can antagonize porcine cellular antiviral defenses. The Erns protein also acts to inhibit interferon production by degradation of viral double stranded RNA produced during viral replication. As the T2 RNase superfamily domain was identified in Erns, it appears likely that PPeV1 degrades viral dsRNA to prevent a cellular interferon response despite its relatively low ~40% a.a. identity to pestivirus Erns proteins.

Two PPeV1 proteins, E2 and NSP2, showed substantial deletions of over 100 a.a. as compared to other pestiviruses with the exception of RaPV1. The cell tropism of pestiviruses is determined by the E2 protein which binds to its receptor CD46. With the exception of NRPV1 and RaPV1, where virus has not been isolated, all pestiviruses are readily cultured in cells in vitro. Despite inclusion of multiple cells lines generally permissive to pestiviruses, we were unable to propagate PPeV1 in vitro. Further experimentation is needed to determine if the substantial reduction in E2 size and only ~30% identity to non-RaPV1 pestiviruses E2 proteins has resulted in a change in receptor utilization.

The finding of a divergent pestivirus that is widely distributed in pigs in the U.S. raises numerous questions. Is PPeV1 a newly emerged swine virus or has it circulated unrecognized for some time? Does PPeV1 infection of swine result in pathology and what clinical symptoms, if any, result? The evolutionary relationship to RaPV1 also draws into question our understanding of the ecology, host range and natural reservoirs of pestiviruses, warranting further investigation.

Example 2

Investigation of Pestivirus as Causative Agent for Pig Intention Tremors

Introduction

In this study, two field cases involving late-onset of intention tremors and mortality were investigated. The samples tested positive for APPV. The first case was from pigs exhibiting intention tremors, resulted in the death of nearly 700 pigs at age of 5-14 weeks from swine farms in North Carolina. The second field case with similar clinical symptoms in 10-16 weeks old pigs occurred in the same production system later that same year. Metagenomic sequencing of brain homogenate from the first field case identified the sample as APPV positive, and the result was further confirmed by quantitative real-time RT-PCR (qRT-PCR). Sera, lymph node, liver and spleen samples also identified as APPV positive by qRT-PCR. The existence of viral antigen (Erns protein) in tissue samples was further confirmed by immunohistochemistry (IHC) using an APPV Erns protein-specific monoclonal antibody. Lymph node samples from both field cases were identified to be positive for APPV by qRT-PCR, IHC and immunofluorescent assay. The data indicate that the novel pestivirus (APPV or APPV-like virus) could be a causal agent of neurological diseases in various aged pigs. The diagnostic reagents and assays developed in this study will be important tools for future control of APPV infection on swine farms.

Materials and Methods

RNA extraction and RT-PCR analysis. Viral RNA from clinical samples were extracted by using the MagMAX™-96 viral RNA isolation kit (Life Technologies) according to the manufacturer's instruction. Quantitative real-time (qRT-PCR) targeted the Erns gene of the virus was performed as previously described (Hause 2015).

Metagenomic sequencing. Pig brain tissues were homogenized in phosphate buffered saline (PBS) and clarified by centrifugation at 6,000×g for 10 minutes. An aliquot of the supernatant was treated with nucleases at 37° C. for 90 minutes to degrade unprotected nucleic acids as previously described (Hause 2015). Viral nucleic acids were extracted using the MinElute Virus spin filter kit (Qiagen) according to the manufacturer's instruction. First-strand cDNA synthesis from viral RNA was performed using the Superscript III first-strand synthesis kit (Invitrogen) using previously described primers (Allander et al., 2005). Sequenase 2.0 DNA polymerase (Affymetrix) was used for second strand synthesis, followed by cDNA purification using the Agencourt AMPure XP beads (Agencourt Bioscience). The double-stranded cDNA was amplified with TaKaRa DNA polymerase (Clontech) using previously described primers (Allander et al 2005). Amplicons greater than 300 bp were purified using Agentcourt AMPure XP beads (Agencourt Bioscience). Amplicons were quantified using a Qubit fluorimeter (Thermofisher) and the Nextera XT library preparation kit (Illumina) was used to prepare sequencing libraries. Pooled libraries were sequenced on an Illumina Miseq instrument using paired 150 bp read chemistry.

Monoclonal antibody production for APPV Erns protein. The APPV Erns-specific monoclonal antibody (mAb) was produced by immunizing BALB/c mice with truncated Erns recombinant protein. The synthetic gene encoding amino acids 20-150 of Erns was cloned into pET-28a vector (Novagen) and recombinant proteins were expressed and purified using the method as we described previously (Brown et al., 2009). BALB/c mice were immunized with 50 ug Erns antigen mixed with Freund's incomplete adjuvant at 2-week intervals for 8 weeks. Mouse splenocytes were fused with NS-1 myeloma cells. Specific anti-Erns mAbs were screened by IFA using MARC-145 cells transfected with the plasmid p3xFLAG-Erns. Hybridomas secreting Erns-specific mAb were subcloned. The clone 96-11 generated the highest antibody titer on IFA was selected for subsequent experiments.

Indirect immunofluorescent assay (IFA). Since there was no APPV isolate available, IFA was developed using MARC-145 cells transfected with the plasmid p3xFLAG-Erns expressing FLAG-tagged APPV Erns protein. The plasmid p3xFLAG-Erns was constructed by cloning the synthesized APPV Erns gene into the pCMV24-3Flag vector (Sigma-Aldrich). Transfection on MARC-145 cells was performed using HD-FuGENE 6 transfection reagent followed the manufacturer's instruction (Roche Molecular Biochemicals). At 48 hours post transfection, cells were fixed in 4% paraformaldehyde and stained with primary mAb 96-11. After lhour incubation at 37° C., cells were washed and then incubated with fluorescein isothiocyanate (FITC) labeled goat anti-mouse (KPL) for additional 1 hour. For IFA on lymph node, slide made from lymph node section of formalin-fixed and paraffin-embedded tissue (see below) was stained with primary mAb 96-11, and then incubated with FITC-labeled goat anti-mouse (KPL) as the secondary antibody. Immunostained cells or lymph node section were imaged with an LSM880 Zeiss confocal microscope (Zeiss). Collected images were processed using Zen 2 and Adobe Photoshop CS3.

Western blot analysis. Cell lysates from transfected or nontransfected control HEK293T cells were lysed in Laemmli sample buffer and samples were heated at 95° C. for 5 min. Proteins were separated by sodium dodecyl sulfate-polyacrylamide gel electrophoresis (SDS-PAGE) and blotted onto a nitrocellulose membrane. The membrane was blocked in phosphate-buffered saline (PBS) containing 5% nonfat dry milk. The membrane was then incubated overnight with primary anti-Erns mAb 96-11 at 4° C. in PBS containing 0.1% Tween-20 (PBST). Following incubation with the primary mAb, the membrane was washed and IRDye 800CW-conjugated goat anti-mouse antibody (Li- Cor Biosciences, Lincoln, Nebr.) was added. The blot was incubated for additional 2 hours at room temperature. Imaging of the blot was scanned under the appropriate fluorescent excitation wavelength using a digital imaging system (Odyssey infrared imaging system; Li-Cor Biosciences). Data were analyzed using Odyssey application software version 4.0 (LI-COR Bioscience).

Immunohistochemistry test. Immunohistochemical staining (IHC) was performed using formalin-fixed paraffin-embedded tissues that were sectioned at 4 μm thickness onto positively charged slides. Slides were stained using the Leica Bond-Max autostainer with the Polymer Refine Red Detection kit (Leica Biosystems) followed the manufacturer's instruction. The anti-Erns primary antibody (mAb 96-11) was diluted to 1:400 with Bond Primary Antibody Diluent (Leica Biosystems). Heat meditated epitope retrieval was performed using citrate pH 6.0 for 20 minutes at 100° C. Tissue sections were incubated with the primary antibody for 15 minutes at ambient temperature. Polymerization was performed with Polymer-AP α-Rabbit (Leica Biosystems) for 25 minutes at ambient temperature. Specific staining was visualized using Fast Red chromogen and slides were counterstained with hematoxylin.

Results and Discussion

Case histories and clinical symptoms. The first field case was reported from nursery to finishing pigs that were originally from three separate sow farms in North Carolina. Initially, five-week-old pigs in two nursery facilities began to show intention tremor symptoms. It was described as "Parkinson's-like" disease. In addition to intention tremors, pigs displayed increased respiration rate. As tremors progressed more seriously, pigs lost the ability to control their movements, including difficulties to walk, standing up and inability to swallow or close their mouths. Mortality was 100% in those pigs demonstrating tremor symptom within four days onset of disease. The first nursery lost 273 pigs and the second nursery lost 173 pigs. The remaining pigs were moved to four separate finishing facilities and new tremor cases continued to develop, resulting in additional death of 247 pigs by 14 weeks of age. A second field case of 10-16 weeks old pigs was reported experiencing similar clinical signs of intention tremors. This group of pigs was also originated from the same sow farms in North Carolina. Again, mortality rate was 100% in those pigs experiencing intention tremors.

Molecular detection of APPV RNA in serum and tissues from pigs experiencing intension tremor. Serum and tissue samples from both field cases were submitted to Kansas State Veterinary Diagnostic Laboratory (KSVDL). Initially, the brain homogenate from a 14 week-old pig showing intention tremor symptom (first field case) was analyzed by metagenomic sequencing. Following subtraction of reads mapping to the host *Sus scrofa*, sequences were assembled de novo into 159 contigs and analyzed by BLASTN. Two contigs were identified as APPV. Templated assembly using the APPV reference strain (Genbank accession KR011347) mapped 195 reads. Where read coverage was sufficient, consensus sequences were extracted and analyzed by BLASTN and showed approximately 87% identity to APPV.

Subsequently, serum and tissues from the first case of pigs were tested using qRT-PCR. Serum, brain, lymph nodes, liver, spleen tissue homogenates were determined to be positive for APPV [cycle threshold (Ct) 33.1-36.9]. The samples from the second case study were similarly analyzed. The results showed that lymph nodes from one pig was positive for APPV by qRT-PCR (Ct=31.5), while other tissues were negative.

Monoclonal antibody development and antigen detection in tissues from pigs experiencing intension tremor. Tissue samples from the first field case were initially submitted to the diagnostic lab of Iowa State University. No significant gross and histopathologic lesions were detected. When the samples were submitted to KSVDL, we also examined the tissue samples in hematoxylin and eosin slides; again, no significant pathological lesion was observed. To test the possibility of existing APPV antigen in those tissue samples, we created a mAb 96-11 that recognizes the APPY Erns protein. The reactivity of the mAb was first tested in IFA using transfected MARC-145 cells that expresses the full-length APPV Erns. MARC-145 cells were transfected with a plasmid DNA expressing pestivirus Erns protein or mock-transfected (control). At 48 hours post-transfection, cells were fixed and stained with anti-Erns mAb and FITC-conjugated goat anti-mouse was used as the secondary antibody. Cells were then stained with DAPI. As shown in FIG. 3A, specific fluorescent signal was detected in Erns-expressing MARC-145 cells using mAb 96-11, but not in MARC-145 control cells. Lymph node section from formalin-fixed paraffin-embedded tissues was also analyzed. Tissue sections are shown from samples identified as APPV positive by qRT-PCR ("LN-APPV infection"), and from a healthy pig, identified as APPV negative by qRT-PCR ("LN-control"), as indicated. The tissue section was incubated with the primary anti-Erns mAb and FITC-conjugated goat anti-mouse was used as the secondary antibody. Nuclei were stained with DAPI. As shown in FIG. 3A, a large number of APPV positive cells were detected and APPV Erns protein was localized in the cytoplasm of virus-infected cell.

Figure 3B:
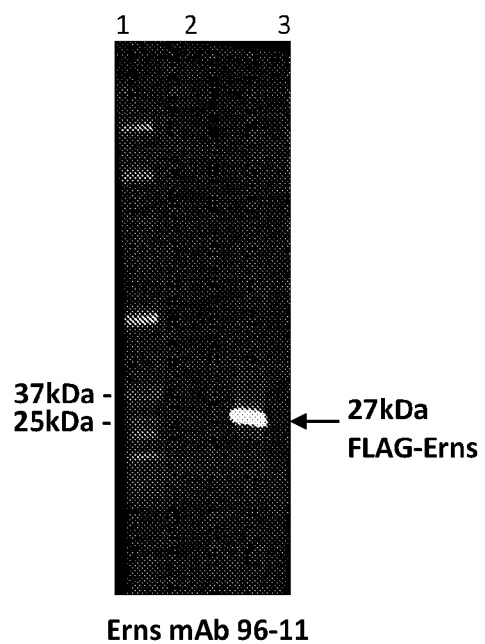
FIG. 3B shows an image from Western blot analysis of HEK293T cells mock-transfected (lane 2) or transfected with a plasmid DNA expressing pestivirus Erns protein (lane 3), and analyzed using anti-Erns mAb. The image was obtained on a digital Odyssey infrared imaging system. The molecular weight marker (Line 1) is shown with red fluorescence.

Specificity of the mAb was further determined in Western blot (FIG. 3B). HEK293T cells were mock-transfected (lane 2) or transfected with a plasmid DNA expressing pestivirus Erns protein (lane 3). At 48 hours post-transfection, cell lysate were analyzed by western blotting with anti-Erns mAb. IRDye 800CW-conjugated (green fluorescence) goat anti-mouse antibody was used as the secondary antibody.

Figure 4:
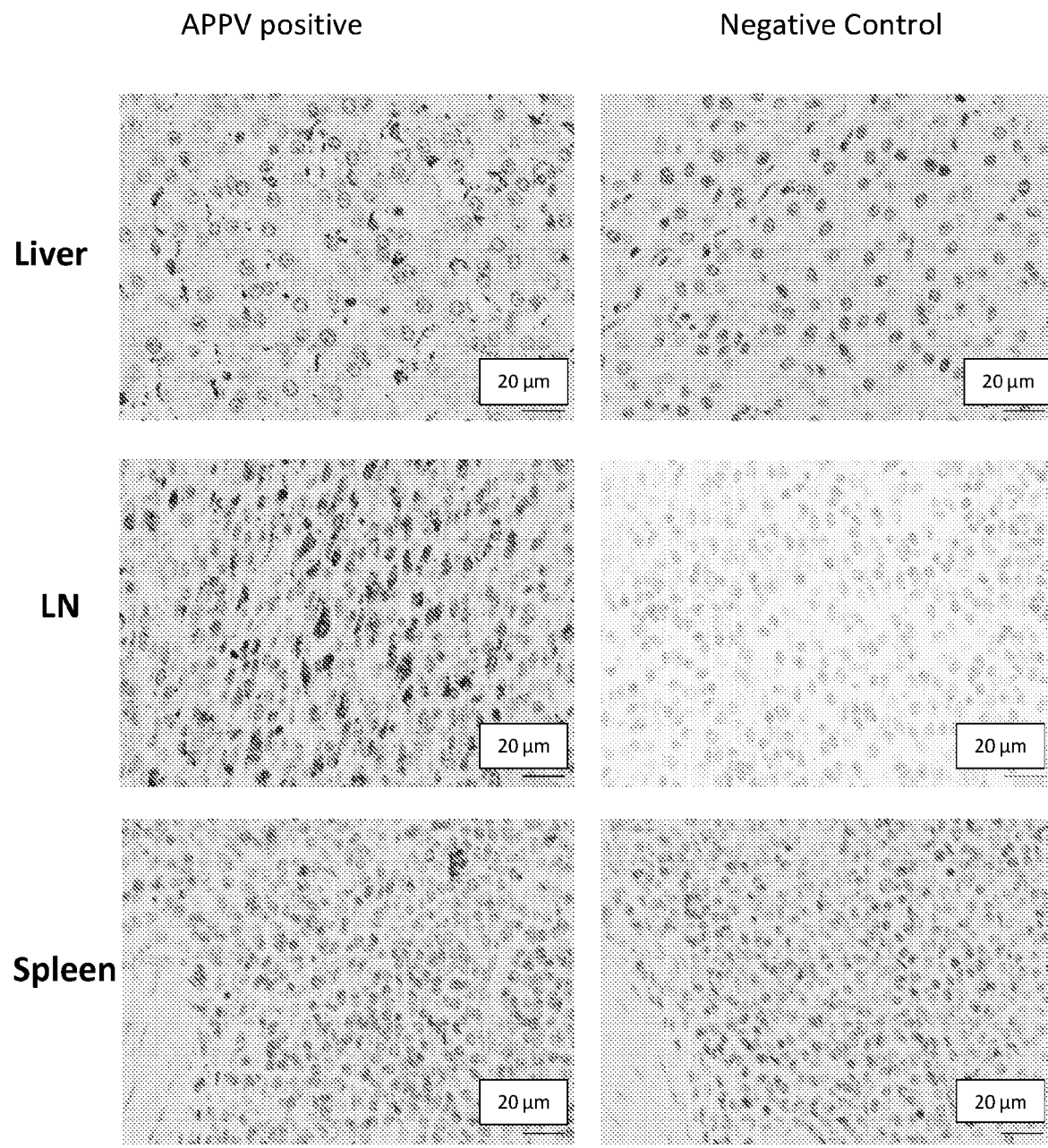
FIG. 4 shows images from detection of APPV antigen by immunohistochemistry test. Immunohistochemical staining was performed on formalin-fixed paraffin-embedded tissues. Tissue sections were from samples identified as APPV positive by qRT-PCR, as compared to tissue sections from a healthy pig, identified as APPV negative by qRT-PCR, as indicated.

Subsequently, this mAb was used to determine the virus distribution in tissues of APPV-infected pigs from first field case. Immunohistochemical staining was performed on formalin-fixed paraffin-embedded tissues. Tissue sections were from samples identified as APPV positive by qRT-PCR, as compared to tissue sections from a healthy pig, identified as APPV negative by qRT-PCR. Slides were stained using the Leica Bond-Max autostainer with the Polymer Refine Red Detection kit (Leica Biosystems). Tissue sections were incubated with the primary anti-Erns mAb and polymerization was performed with Polymer-AP α-mouse. Colors were developed using Fast Red chromogen and slides were counterstained with hematoxylin. The IHC result showed that the viral antigen Erns was detected positive in the liver, spleen and lymph nodes, but was negative in the brain tissue (FIG. 4). We further used the mAb 96-11 to conduct IFA on tissue samples from the second field case. The result showed only the lymph node sample was positive for APPV Erns antigen among all the tissue samples, including brain, liver, kidney, spleen, intestine, and spinal cord (FIG. 3A, bottom panels).

The study present here is based on two separate outbreaks of disease typified by uncontrollable intention tremors, which led to 100% mortality in pigs shown the symptom. The finding of APPV RNA in the brain of a 14 week-old pig experienced intention tremor suggests that APPV is the causal agent for such disordered neurologic disease. The data suggests that APPV as a viral agent causative of neurological disease in pigs. Our data indicate that APPV distributed in many tissues/organs of pigs, including brain, lymph nodes, liver, and spleen. Although both metagenomic sequencing and real-time RT-PCR detected positive for APPV in brain tissue, IHC was negative for the viral antigen. The negative IHC result is most likely caused by lower amount of antigens being present in brain tissue, since the lower amount of APPV RNA was detected by qRT-PCR (Ct value of 36.9). Compared to other tissue samples, the lymph nodes were consistently identified as APPV-positive in pigs from both case studies using qRT-PCR, IFA and IHC, which suggests the lymph node may be one of the sites for viral persistence. Furthermore, the results from both antigen detecting tests (IFA and IHC) are consistent with that of qRT-PCR results, indicating these tests and reagent (anti-Erns mAb) are reliable in clinical diagnosis of APPV infection; and they will be important tools for future control of APPV infection on swine farms.

The invention claimed is:

1. An immunogenic composition to induce an immune response against porcine pestivirus infection in a pig, said composition comprising a therapeutically-effective amount of atypical porcine pestivirus (APPV) antigenic agents dispersed in a pharmaceutically-acceptable carrier, said APPV antigenic agents being selected from the group consisting of: (a) isolated whole virus having an mRNA complementary coding sequence according to Genbank accession no. KR011347.1 (SEQ ID NO:1) that is a live attenuated or inactivated virus, (b) functional fragments of said isolated whole virus selected from the group consisting of virus subunits, purified antigens, surface proteins, recombinant viral proteins and combinations thereof, and (c) combinations of the foregoing, wherein the functional fragments and combinations thereof further comprise an adjuvant.

2. The composition of claim 1, wherein said virus is an APPV isolate comprising a gene according to SEQ ID NO:3 encoding for an Erns protein.

3. The composition of claim 1, wherein said virus is an APPV isolate presenting an Erns epitope according to SEQ ID NO:4.

4. The composition of claim 1, wherein said functional fragments are coupled to a carrier protein.

5. The composition of claim 1, comprising a combination of at least two different APPV antigenic agents.

6. The composition of claim 1, further comprising an adjuvant, selected from the group consisting of aluminum salts, potassium aluminum sulfate, mixed aluminum salts, peptides, oil or hydrocarbon emulsions, and combinations thereof.

7. A method of vaccinating a pig to induce an immune response against porcine pestivirus infection, said method comprising administering an immunogenic composition according to claim 1 to said pig.

8. The method of claim 7, wherein said administering is selected from the group consisting of:

injecting said vaccine composition intramuscularly, subcutaneously, intradermally, or intravenously using a needle and syringe, or a needleless injection device; and mucosal administration nasally or orally.

9. A kit for inducing an immune response against porcine pestivirus infection in a pig, said kit comprising:

an immunogenic composition according to claim 1; and instructions for administering said composition to said pig.

* * * * *

SEQUENCE LISTING

```
<160> NUMBER OF SEQ ID NOS: 10

<210> SEQ ID NO 1
<211> LENGTH: 11276
<212> TYPE: DNA
<213> ORGANISM: Porcine pestivirus 1 strain 000515
<300> PUBLICATION INFORMATION:
<308> DATABASE ACCESSION NUMBER: GenBank/KR011347.1
<309> DATABASE ENTRY DATE: 2015-07-29
<313> RELEVANT RESIDUES IN SEQ ID NO: (1)..(11276)

<400> SEQUENCE: 1
gcagatatcg gtggtggacc tgggggttgg gctcaccgtg ccccttcatg gggtagacct      60
cactgcttga tagagtgccg gcggatgcct caggtaagag tataaaatcc gttgttcact     120
aacatggaaa aacagattgc atactattta aaaaaagaaa aacaaagaaa tgggtggaca     180
gaactggtgg taggagaaag ctatacgaaa ataaccacac tctctggaaa aacctatcga     240
ggtacttggg aaatggagaa gcggtcaaat ccttatggaa cctaccttcc cagacctagt     300
cctcaacagc tcactgccat acaccccac cccgtggtga attgtaaggt gatggagtac      360
aaggagaagg accctaatta tggcgattgc ccgaatacga atgggtgtt tatcgatgaa      420 aagggtagaa ggctgagtag cccccccattg ggtatctgga agataagatt ggattatggt    480
gatctggtaa atatagacag accaattcct gctagtggga aaaactctta tcgagtcgag     540
acctgtagcg gagagctggc caccgtaaca ctgacacacg ataggtact tgtggaagac      600 tacaggggac tttaccaatg gaaacccaac tgtgaaggaa tggtgctcta cgtgaaaact     660
tgttctgatt gggcagacca ggtggaaaaa caggagaagg aaagcccccc gaaacctcag     720
cgaccaccaa ggcgggatcc ccgaaaagga ttacaaccac aagtccccaa agaaactgag     780
gtcacagaaa agaagagaca acctagtgtc actttagtgt caggggggaca gaaagcccag     840 gtcatctata aaggtaagac taaaaacaaa aagacaccgg atggagtcta taagtatcca    900
ggagctagag aaggggatgt agtaaaggtc aggaagatgc tgaagaactg gcatatagcc     960
ttagtaatgt acttaatata tattataact ccaagttttg ccaaggtcca gtggtttta    1020 aaggatgaaa attcgtcagg aattaaccag gtattatgga gaagacagat caacagatcc    1080
ctacatgggg agtggcctaa ccagatttgc catggcatgc caaatgaaac tatcactgac    1140
gaggaattac gcagtttagg aatgatagat acaagcccta gaacaaacta tacttgctgt    1200
cagttgcaat atcatgaatg gagaaacat ggttggtgca attacccaca aaaacaggct    1260
tggatcagga gaatagcgac cctgcaagcc aacctcaccg gagcttataa gggacctgag    1320
tgtgctgtca tctgtcgatt taacggcacc tataacattg tgagacaggc cagagacgag    1380
gtgagtccac tgcagggtg taaggaaggg caccctttc tattttctga ggaaaggtcc      1440
gacacctcgt gcttgaggcc gccctccact agttgggtga gaccagtgaa aatggatgag    1500
gcatcgatgg ctgacagctt cgcccacggg gtcgataagg ccataatatt aatcagaaaa    1560
ggggcatcgg gaattatcaa tttcctagac actattggga gatggttacc ggtgactgaa    1620
```

```
gcagctatag taccatattg cgaaacctac actgtgacag ggatgtatgt ccatgtaaag    1680
aattgtcttc ctagagggct acctaagcat tcaaaaataa tctccccaac aatgatatac    1740
ctgggggaag gcgacccggc ccataacatc cagcacttat tcggctcagg tatagcaaag    1800
tgggtcctag tcttactcgg gatcctgggt gagtggtatg gagaattagc ctctacaatt    1860
tacttactac ttgagtatgg gtctgagtgg ttggaacatg aaagtctggt cacagaaggg    1920
ctgttcccgg gtattaatat tacaatagac ctcccggcta gccacacagt acctggttgg    1980
gtgtgggtcg cgggccagtg ggtatgcgtg aagccagatt ggtggcccac acaggtctgg    2040
atcgaaaccg tggtggcaga agcctggcac atattaaaaa tcctagcatc ggccttggtg    2100
aatatagtca ctgcatttgt gaacctagaa ctggtctatt tggttataat actagtcaag    2160
atatcaaagg ggaacttgat aggtgccata ttatggtgcc tgttactgtc tggggctgag    2220
gggtcgtgtc taaaaaggca agactactac aacgtccagc tagttgtcga agaaaagact    2280
ggcgtagaaa aacggtctat aatgggcaag tggacagtga taactaagga aggccaggaa    2340
ccaagattaa tggagcagat aaagatggtg tcaaataaaa gtgtgacaga aatttactgc    2400
tataatgggc tcaatactag cagttggggg cggcaaccga caaaacagag agggtgtagc    2460
caaatagtgc cctattggcc tggtgacaat gtcctagaaa acaatactaa tagcacgggt    2520
tactgggtga acgcaacagg cagctgtcag cttagggaag gcgtatggct atcaagaaag    2580
ggcaatgtac ggtgccagcg taatggcaca tccttgatac tgcaactggc gataaaagaa    2640
gacaatgaca ctatggaaat accgtgcgac ccagtggaaa cagaaagcat gggtcctgtg    2700
gcacagggta cttgcgtgta cagctgggca gtcgctccaa gagggtggta ctataatagg    2760
aaagatggtt actggctgca gtatataaag aaagatgact accagtactg gactaaaatg    2820
cctactgcct cgtctgcagc aacaatgtac cgccatctgc ttcctttatt ggtggcctgc    2880
ctcatgggcg gcaggatatc ggtgtggatt gtcgcaatgc tcctatctct acaggtggaa    2940
gctagtgaag tgggcactaa gcaactggcc gtcacactaa ctctatggaa aatggactgg    3000
acggaattac tcttctacat catcataatg ttagccgtca aggaagacct cataaagaaa    3060
atagtgactc caagccttgt aaccttgaaa aatagtccag tagccttgag ctttctcatt    3120
gtactcaggc ttgtgggggg cagcgaagca ctcccagtgg gcttactact agaaaaaatg    3180
tgcatagacc aaccagagtt tggaactccc ttcttgatct acttgtggga caattggaaa    3240
tggactgtcc tagtcagttt ctctgcacta atccatgaaa aaactataag actggcaagg    3300
aagctgctat ggcaacaca tataacgcg ctcacgttga ctggtctaag tgattcaatt    3360 tttatatca tgcttataat gactaaccta ttaataaaga cattcatata tctattgggg    3420
gtcagcataa attgggttga aaagaaaaa aagaggttac tagtaaagag gaagctaata    3480
tataagaaaa ccgcaatctg taatcaggac gagaatgaat tggagaacaa gttcaacaag    3540
atatccgtta atgcggactt caccccatgc aagcttgaat tattacaact actcagggct    3600
tttttagttt ccctatgttt ttcctactac aaaccccctcc tgtatgcaga gactacccta    3660
actgtcatag taattggcgt gcaggaatac aatgtggcaa tggcacgtgg gcgaagcgtg    3720
gttcataaat tattagccat ggcatattat gtatatggtc acatacaggg caatatgttc    3780
cagctcgcca gtatccagtg cctgttgtca agcccaagga aaatcatgaa acatatgata    3840
gaaaacccaa tccttaggaa gttctggcaa ggtgaaacag aactctacaa ccagggtgtc    3900
aatcaatcta aaatagtaaa cccaagaaa atcgggctgg aagaattaca taaaggtatg    3960
tgcggcctac caactgtagt acaaaatttg gtcatatatg caaagaagaa tgactctctt    4020
```

```
atattaggag aattgggcta tcccccctggg gatctcacca gtgatgggtg ggaaatttta      4080
ggccccggca gaattccgaa gatcaccaat gttgagtctg ccaagatgga cttactctcc      4140
aaactcatga cctttctggg gattgaaagc tcaagagtcc ccagaacccc aatccactca      4200
acaaggaaat tactgaagat agtgagaggc ttggaaactg ggtgggggta cactcacgca      4260 gggggggatta gtagtgcaaa acatgtcaca ggtgaaaaaa acttaatgac ccacatggag      4320
ggcaggaagg gcaagtacat cttacaatcc caagaacatg gtgccgatga ggtagagtat      4380
ggagtaaaaa ctgaccaaag agcgcccgac aacgccttat gttactgctt taaccctgaa      4440
gccacaaaca taaagggaga aacagggggcc atggtgttca tgaaaaagat aggaaaaaaa      4500
tggacccttg taacatcaga tggtaacaaa gcctactata atgtaaacaa tctgaaaggg      4560
tggtccggac taccaataat gctgcactcc accggggcca tagtagggag gattaaatcg      4620
gcatattcag atgaaaacga cttggtggag gagcttatcg actccaggac tatcagtaag      4680
agtaatgaga caaacctgaa ccaccttatt aaggaattgg cagatatgcg gagggggggag      4740 ttccgctcaa ttacccttgg aacgggtgct gggaaaacca cagaactgcc caggcaatat      4800
ctcacaacag taggtacaca taaatctgta ctagtcctgg tccctctaaa agcacccgcc      4860
gaaagtgtct gccgcttcat gaggtctaag tacccctacca ttaacttttc tttaagagtg      4920
ggagagcgga aagagggaga cgtgagcagc ggtatcaccct atgctactta cggattttgc      4980
tgccagctta acctagttca actcaaagag tggatatcca ggtactcaat ggtgttttttc      5040 gacgaatacc acacggcaac cccggaacag atagctataa taagcaagat ccacgcactg      5100
aaagttaaaa ccaggatagt ggccatgtca gcaactcccc cgggcaccgt gacaactgaa      5160
ggcaggaaat ttgacatcga agaagtcggg gttgccacaa tagagaaggg agaggaacca      5220 aaaaggggggc gtgtagcggt cgccggcatg caggtcccgt tggaagattt gacagggaag      5280
aattgcctgg tattcgtggc aaccaaagaa gccgcggaga cggaggccaa agagctgcgt      5340
gccagaggaa tcaacgcaac ctattactat cgaggtatag accccaaaaaac tctggaacat      5400 gggatgacca accagccata ttgtattgtg gccacaaatg ccatcgaatc gggcataacc      5460
tgtcctgatt tagatgtggt catagatacc atgcagaaat acgaaaaggt agtgaatttc      5520
tcagcaaaga tgcccttgat tgtcacatca ttagtaaaga aaaaaatcac cagggaagaa      5580
cagggccaga ggaaaggtcg agtgggcagg caaaagaagg gaaatatta ttatccttcg      5640 ggggtggtac cgaatggatc aaaagacctt agctatctaa tcctgcaggc ccaagagtat      5700
ggtgtcctgg aacaagttaa cataacagag tacttcataa aatgaatga ggactggggt      5760 ctttacgacg tagatgaggt agaagtgaga atactggaga gaatgaacaa ggaaatcttg      5820
cttccgctag gcatcgtgga gaagcaaatc ctggaaagaa gtactcaccc ggaaaaggtg      5880
gcactgttgt ataataaatt agtacaaaaa agccccatag tatacccctag agtgcaggag      5940 ggtgaggtta gtaaggaata taatacccac aatctggccg tgtatgacaa gctaaaagat      6000
gtcaatccac aggccattta tgtcctagca gaggaggaaa gagccacaga gatgatggc      6060 ctcgagttcg aacaagatcc atccgactta caggattcag tagtccaact ttgtgaagac      6120
atcaagaggt atacaaaaact ctctgggatc actgagaaat tactagtagg tacaatggtg      6180
gggtacatag gatataaagc cctaaccaga aaccacgtgc cctgggttag taaagagtat      6240
tgctatgagc tgactgattc acctgatact tacgagaact catttgcacc tttagatgtc      6300
gatatccaaa accccggtga aagtaaacac ccagaacaac tggcagatca tcaactgagg      6360
```

```
caattactgg agactgggag agacaaggca atcgacttcc taaaaggagt ccgcgagttc    6420
actagtgggg ctataaatag cccaaaagca ctgagtatat gggagaaaat atatcagtac    6480
ttgaggaaac atcagggcga gatcatctca tcagcggcgt ggggcagcgc aacggccctt    6540
cacgacagta tcaaatctag gttaggggat gaggtagcca ccgcagtaat aattcttaag    6600
tatttagcat ttggtgaaag agaattgtcc ggactgacca ggcaagtctt aattgacatc    6660
atagtatatt atatagtcaa caagccccgg ttcgaaggag atgactatgc gaagagaaag    6720
gggagaagac tggtcattga agtcttgatg ggggcactgg caacttatgc agtgtcaaat    6780
ttttggggcg tgtctgttaa taagatacta caaccaatat ctgattatct accttatgct    6840
accgccactt tagctttcct tcgcccaact ttcatggaat cagcggtggt ggtcgcttct    6900
tctatttaca gagcctttct ctccattaaa catgcagaaa acaggagtct cgttacgcag    6960
gtcgcctctg ccgtcttga agtcatgggt ttgacccag tatcagctgg cctaggcgtc    7020
ctgctgggc ttgggctgtg tgtgctccat atgaacattg acaagaatga ggagaagagg    7080
acactgatat tgaaaatgtt tgttaaaaac tttatagacc aggcagcact agatgagtta    7140
gacaaactgg agccagaaaa aataatcctc tcattgttgg agggcatcca aacttgcaca    7200
aacccaatca gagctattat gattttatac agagtgtatt acaagggaga atcgtttaca    7260
gaagccttgt ctaagatggc tggaaagtcc ctcatagtga tggtcattgt cgagttcctg    7320
gaactgacgg gccagaccca aggggggtat atagacctta gtgccaatct gctgactttt    7380
cttttggaaa aactgaaaaa gatgaccaac ctcgccatag gggaggccag aaaggcctta    7440
ctccctattc catacttgta ctgtgaaacc tggcagtctg acgccagaat caaggccccg    7500
gaatcctacg accaggtggc agtggaatgc agatgcggtg cttccgcaag atactccttt    7560
caccacgggg ttcatgaggt attggaagaa aaaatgacca agtggtgtaa gaacttcttc    7620
ctatggggac ctaatttttc caacccggat ccaaagagga tgacattcta tgaatgcggt    7680
caagcaagaa agtgtcccgt aatcataatg ggcgaagaca taacctttgg taaatatggt    7740
atatatgtca aatttggcca cgggcctgat gggagaagat taataagggg caccacccat    7800
gccaccatca gcagggagga gctgctagaa atcctaacgg ccccaagtca gtagcaata    7860
ggtaaagtca agctgacaga ttactgcaat caaaagggaa tgatagatag gaaactggct    7920
gtacttgaag gtgacaaaat acatttctgg aaagcacatc gtgggtccaa gatcacggat    7980
caactcacca ttgagagtct gacagatgac ttggggtcgg aaatcaggga tatcacatgg    8040
gagctgtaca caggtgggac atgcaccgta aaaggaatat cccttaggtc gtgcgcacca    8100
gggcaacgaa acaaggccac ggttttgtgt gattgtaccg atgtgctaag cccctgctat    8160
ctaattaatg gcaggagacc atccccgttt gacgtcgtag aaggttatga gtgccaccat    8220
cggaagcctc gagcgacgta tgaagaccta gagatggaag aaatactaaa gagacgggtt    8280
cctgtctacg accctctttg tctgttcgac attgacagta aactactgcc tcccgacact    8340
tattatttgg aagaggatcg agaagacttt gagtatgcgt tgaggtgctg gggcctcggg    8400
gtttatgtag tggacgggtc cgtcacttcc cccccagata taagaataca ccacagctcc    8460
gtactgctgc tactgacacc tggagtggac tctgagctac acttgcagta tatactttgt    8520
tactctcacc aggcagaggt ggatatctac attagggtc aacttctaga ggaggaaaat    8580
actgccacgg aagcggaagg cttttcagga ggcggtgatg aagggacggg tgacgtggtg    8640
gcagaagatg aggacacgtt gtccacaaca gaatcaatac cccgctaga agaggaagaa    8700
ggaggtggag agctaattac ctatgtggtt atcaggggat tgcaagaaga aagatacact    8760
```

```
agccatctca aattgaatga ctggatcagt gaaaatattt cggagccaca tagagtccaa    8820
atcatgcttg acggaacagt gagagtcaca ataaaagagg gcaaagtgaa acacctattt    8880
ggggtctaca gaatagagaa ctccctggaa gcaatgttca aagagaccat agctgacctc    8940
cccacagcca cccaaccgcc cagagggccg atctacacgg ccaaagaatt ggcccagggg    9000
aatattgccc cagtccaacc tgcagcaaat tattatggaa tgatagaggg gagaggggac    9060
ccgatgacag cgttcgaagc cttatcggtc ctgcggtcac aaaaagtctt agccaaggaa    9120
gtgaaaataa gtactcgcaa ggcacaggct tttctaaata aagtcaggag aactgctgag    9180
atcagggcct cggaattggc attaaaacgc ttaccggtac tcggaaaaat aaatgggaga    9240
aaattgatta gagaggaaac taatatcccc aaccaaaggt tggcatcgat aatgacttca    9300
ataggaatca gattagagaa actgccggtg gtcagagcaa acacctccgg ccctaagttt    9360
aggcaatcaa tcttagaaaa aatggataaa tatgaaaatg aacaagttcc agagttacat    9420
gagaagatgt gggcggcttt tctggtgacc gcccgacaag acttaagaaa tacatatgag    9480
gaagtaactt accctgaact ggagatcgga atcaaccgga agggagcacc aggttttttt    9540
gaaaaagaaa gttcaatagg agaggtactg gaaaagaagg aaaaaattga tgtcgtgatc    9600
cgagagattg aaaagggcac tcacttatat tacgaaacgg ccatgccaaa aaatgagaaa    9660
agagatgtgc ttgatgattg gttgtcagag gatttcgtca cttacaagaa accacgtgtg    9720
atacagtacc ctgaggcagt cacccgattg gccatcacca aaataatgta caagtgggta    9780
aagcagaaac ctgtagtgat ccctggctat gaggggaaaa ccccgatttt tgaaatattt    9840
gaaaaagtta gtgcagattg ggctcagttt aaaaacccag tagcagtcag cttcgatacc    9900
agggcctggg atactcaagt aacgagagag gacctcaaac tggtagggcg gatacagaaa    9960
tattactaca aaaagaaata ttggaaattc attgacaact tgactaccat gatggaggaa   10020
gtgcccgtaa tcactgtaga aggagacatg tttctcaggg tcggacaacg cgggtctgga   10080
cagcccgaca cctcagcagg taattccata ttaaacgtgc taacaatgct agtagctttc   10140
tccgaatcta caaacttgcc catagcagct gcctggaggg cctgtcgtat ccacgtctgt   10200
ggagatgacg gctttctaat cacagaatca gaattaggga ggaaattcgc tgaaaaaggt   10260
gtccccttgc tagcttcatt cggcaaaccc caaaaaatca ctgagggggc aagcttaaag   10320
ataactagca actttgatgg aatagagttt tgcagccact cccccatcag agtccaaaca   10380
ccaaacataa ggtggatgcc ggcgaggccc acagcaacaa ttctagggaa aatgagtacc   10440
aggctgggtg agggtgccac cagatcggga gaagagtatg aaaagcaggt ggcattcgca   10500
tacttactga tgtaccccct gaatccactg attaggagaa ttggcctcct attgctatca   10560
actactgacc ccatggggaa agaggaaacc ccgtgttctg acgagggggt gaaatatgtc   10620
ggggatccta ttgccgcata cagggatgta tgggggcaca aattagagga tgtagggcat   10680
gtcgatcagt cgcagttatc ccggatgaac tatagcatga cttacttagg gatctggaaa   10740
ccaaagacga gccagcgact agtcgaacag tgctgtcggc tggccgagaa aaacaattgt   10800
gtggcacgtg cagattctct aattaagaaa aaggtcaaga tcacctatga cccggggata   10860
ggagcggctc aagttattcg taggtgggaa gagctggagt ggaccagaag gaaacccgaa   10920
ttcaccaaag taactgcgga agatgacctc ttcctagtcc tttttaagag actgtcaaag   10980 tacattttc agaaaattaa gttcatgcag aagatgttca cccttatta gtgggggc     11040 gcttatttaa atgcagccag tatctggtgg gtataagact tgtgtgaata aaatatacaa   11100
```

-continued

```
ctgaaagggg caagtggccg tataggctgg ggcgatcgcc gtaccccccc tttaccaggc    11160
gcctcaaccc catgtaccat ggggttgttg taaatacttg aatgaatgga gtaatacggg    11220
taatggactt acaagccagt attgccccat ttgctttata gtggtgacga gatatc        11276
```

<210> SEQ ID NO 2
<211> LENGTH: 3635
<212> TYPE: PRT
<213> ORGANISM: Porcine pestivirus 1 strain 000515

<400> SEQUENCE: 2

```
Met Glu Lys Gln Ile Ala Tyr Tyr Leu Lys Lys Glu Lys Gln Arg Asn
1               5                   10                  15

Gly Trp Thr Glu Leu Val Val Gly Glu Ser Tyr Thr Lys Ile Thr Thr
            20                  25                  30

Leu Ser Gly Lys Thr Tyr Arg Gly Thr Trp Glu Met Glu Lys Arg Ser
        35                  40                  45

Asn Pro Tyr Gly Thr Tyr Leu Pro Arg Pro Ser Pro Gln Gln Leu Thr
    50                  55                  60

Ala Ile His Pro His Pro Val Val Asn Cys Lys Val Met Glu Tyr Lys
65                  70                  75                  80

Glu Lys Asp Pro Asn Tyr Gly Asp Cys Pro Asn Thr Asn Gly Val Phe
                85                  90                  95

Ile Asp Glu Lys Gly Arg Arg Leu Ser Ser Pro Pro Leu Gly Ile Trp
            100                 105                 110

Lys Ile Arg Leu Asp Tyr Gly Asp Leu Val Asn Ile Asp Arg Pro Ile
        115                 120                 125

Pro Ala Ser Gly Lys Asn Ser Tyr Arg Val Glu Thr Cys Ser Gly Glu
    130                 135                 140

Leu Ala Thr Val Thr Leu Thr His Asp Arg Val Leu Val Glu Asp Tyr
145                 150                 155                 160

Arg Gly Leu Tyr Gln Trp Lys Pro Asn Cys Glu Gly Met Val Leu Tyr
                165                 170                 175

Val Lys Thr Cys Ser Asp Trp Ala Asp Gln Val Glu Lys Gln Glu Lys
            180                 185                 190

Glu Ser Pro Pro Lys Pro Gln Arg Pro Pro Arg Arg Asp Pro Arg Lys
        195                 200                 205

Gly Leu Gln Pro Gln Val Pro Lys Glu Thr Glu Val Thr Glu Lys Lys
    210                 215                 220

Arg Gln Pro Ser Val Thr Leu Val Ser Gly Gly Gln Lys Ala Gln Val
225                 230                 235                 240

Ile Tyr Lys Gly Lys Thr Lys Asn Lys Lys Thr Pro Asp Gly Val Tyr
                245                 250                 255

Lys Tyr Pro Gly Ala Arg Glu Gly Asp Val Val Lys Val Arg Lys Met
            260                 265                 270

Leu Lys Asn Trp His Ile Ala Leu Val Met Tyr Leu Ile Tyr Ile Ile
        275                 280                 285

Thr Pro Ser Phe Ala Lys Val Gln Trp Phe Leu Lys Asp Glu Asn Ser
    290                 295                 300

Ser Gly Ile Asn Gln Val Leu Trp Arg Arg Gln Ile Asn Arg Ser Leu
305                 310                 315                 320

His Gly Glu Trp Pro Asn Gln Ile Cys His Gly Met Pro Asn Glu Thr
                325                 330                 335

Ile Thr Asp Glu Glu Leu Arg Ser Leu Gly Met Ile Asp Thr Ser Pro
            340                 345                 350
```

```
Arg Thr Asn Tyr Thr Cys Cys Gln Leu Gln Tyr His Glu Trp Lys Lys
            355                 360                 365

His Gly Trp Cys Asn Tyr Pro Gln Lys Gln Ala Trp Ile Arg Arg Ile
    370                 375                 380

Ala Thr Leu Gln Ala Asn Leu Thr Gly Ala Tyr Lys Gly Pro Glu Cys
385                 390                 395                 400

Ala Val Ile Cys Arg Phe Asn Gly Thr Tyr Asn Ile Val Arg Gln Ala
                405                 410                 415

Arg Asp Glu Val Ser Pro Leu Thr Gly Cys Lys Glu Gly His Pro Phe
            420                 425                 430

Leu Phe Ser Glu Glu Arg Ser Asp Thr Ser Cys Leu Arg Pro Pro Ser
        435                 440                 445

Thr Ser Trp Val Arg Pro Val Lys Met Asp Glu Ala Ser Met Ala Asp
    450                 455                 460

Ser Phe Ala His Gly Val Asp Lys Ala Ile Ile Leu Ile Arg Lys Gly
465                 470                 475                 480

Ala Ser Gly Ile Ile Asn Phe Leu Asp Thr Ile Gly Arg Trp Leu Pro
                485                 490                 495

Val Thr Glu Ala Ala Ile Val Pro Tyr Cys Glu Thr Tyr Thr Val Thr
            500                 505                 510

Gly Met Tyr Val His Val Lys Asn Cys Leu Pro Arg Gly Leu Pro Lys
        515                 520                 525

His Ser Lys Ile Ile Ser Pro Thr Met Ile Tyr Leu Gly Glu Gly Asp
    530                 535                 540

Pro Ala His Asn Ile Gln His Leu Phe Gly Ser Gly Ile Ala Lys Trp
545                 550                 555                 560

Val Leu Val Leu Leu Gly Ile Leu Gly Glu Trp Tyr Gly Glu Leu Ala
                565                 570                 575

Ser Thr Ile Tyr Leu Leu Leu Glu Tyr Gly Ser Glu Trp Leu Glu His
            580                 585                 590

Glu Ser Leu Val Thr Glu Gly Leu Phe Pro Gly Ile Asn Ile Thr Ile
        595                 600                 605

Asp Leu Pro Ala Ser His Thr Val Pro Gly Trp Val Trp Val Ala Gly
    610                 615                 620

Gln Trp Val Cys Val Lys Pro Asp Trp Trp Pro Thr Gln Val Trp Ile
625                 630                 635                 640

Glu Thr Val Val Ala Glu Ala Trp His Ile Leu Lys Ile Leu Ala Ser
                645                 650                 655

Ala Leu Val Asn Ile Val Thr Ala Phe Val Asn Leu Glu Leu Val Tyr
            660                 665                 670

Leu Val Ile Ile Leu Val Lys Ile Ser Lys Gly Asn Leu Ile Gly Ala
        675                 680                 685

Ile Leu Trp Cys Leu Leu Leu Ser Gly Ala Glu Gly Ser Cys Leu Lys
    690                 695                 700

Arg Gln Asp Tyr Tyr Asn Val Gln Leu Val Val Glu Glu Lys Thr Gly
705                 710                 715                 720

Val Glu Lys Arg Ser Ile Met Gly Lys Trp Thr Val Ile Thr Lys Glu
                725                 730                 735

Gly Gln Glu Pro Arg Leu Met Glu Gln Ile Lys Met Val Ser Asn Lys
            740                 745                 750

Ser Val Thr Glu Ile Tyr Cys Tyr Asn Gly Leu Asn Thr Ser Ser Trp
        755                 760                 765
```

```
Gly Arg Gln Pro Thr Lys Gln Arg Gly Cys Ser Gln Ile Val Pro Tyr
770                 775                 780

Trp Pro Gly Asp Asn Val Leu Glu Glu Gln Tyr Tyr Ser Thr Gly Tyr
785                 790                 795                 800

Trp Val Asn Ala Thr Gly Ser Cys Gln Leu Arg Glu Gly Val Trp Leu
                805                 810                 815

Ser Arg Lys Gly Asn Val Arg Cys Gln Arg Asn Gly Thr Ser Leu Ile
            820                 825                 830

Leu Gln Leu Ala Ile Lys Glu Asp Asn Asp Thr Met Glu Ile Pro Cys
        835                 840                 845

Asp Pro Val Glu Thr Glu Ser Met Gly Pro Val Ala Gln Gly Thr Cys
850                 855                 860

Val Tyr Ser Trp Ala Val Ala Pro Arg Gly Trp Tyr Tyr Asn Arg Lys
865                 870                 875                 880

Asp Gly Tyr Trp Leu Gln Tyr Ile Lys Lys Asp Asp Tyr Gln Tyr Trp
                885                 890                 895

Thr Lys Met Pro Thr Ala Ser Ser Ala Ala Thr Met Tyr Arg His Leu
            900                 905                 910

Leu Pro Leu Leu Val Ala Cys Leu Met Gly Gly Arg Ile Ser Val Trp
        915                 920                 925

Ile Val Ala Met Leu Leu Ser Leu Gln Val Glu Ala Ser Glu Val Gly
930                 935                 940

Thr Lys Gln Leu Ala Val Thr Leu Thr Leu Trp Lys Met Asp Trp Thr
945                 950                 955                 960

Glu Leu Leu Phe Tyr Ile Ile Ile Met Leu Ala Val Lys Glu Asp Leu
                965                 970                 975

Ile Lys Lys Ile Val Thr Ala Ser Leu Val Thr Leu Lys Asn Ser Pro
            980                 985                 990

Val Ala Leu Ser Phe Leu Ile Val Leu Arg Leu Val Gly Gly Ser Glu
        995                 1000                1005

Ala Leu Pro Val Gly Leu Leu Leu Glu Lys Met Cys Ile Asp Gln
        1010                1015                 1020

Pro Glu Phe Gly Thr Pro Phe Leu Ile Tyr Leu Trp Asp Asn Trp
        1025                1030                 1035

Lys Trp Thr Val Leu Val Ser Phe Ser Ala Leu Asn His Glu Lys
        1040                1045                 1050

Thr Ile Arg Leu Ala Arg Lys Leu Leu Leu Ala Thr His Ile Thr
        1055                1060                 1065

Ala Leu Thr Leu Thr Gly Leu Ser Asp Ser Ile Phe Tyr Ile Met
        1070                1075                 1080

Leu Ile Met Thr Asn Leu Leu Ile Lys Thr Phe Ile Tyr Leu Leu
        1085                1090                 1095

Gly Val Ser Ile Asn Trp Val Glu Lys Glu Lys Lys Arg Leu Leu
        1100                1105                 1110

Val Lys Arg Lys Leu Ile Tyr Lys Lys Thr Ala Ile Cys Asn Gln
        1115                1120                 1125

Asp Glu Asn Glu Leu Glu Asn Lys Phe Asn Lys Ile Ser Val Asn
        1130                1135                 1140

Ala Asp Phe Thr Pro Cys Lys Leu Glu Leu Leu Gln Leu Leu Arg
        1145                1150                 1155

Ala Phe Leu Val Ser Leu Cys Phe Ser Tyr Tyr Lys Pro Leu Leu
        1160                1165                 1170

Tyr Ala Glu Thr Thr Leu Thr Val Ile Val Ile Gly Val Gln Glu
```

-continued

```
            1175                1180                1185

Tyr Asn Val Ala Met Ala Arg Gly Arg Ser Val Val His Lys Leu
        1190                1195                1200

Leu Ala Met Ala Tyr Tyr Val Tyr Gly His Ile Gln Gly Asn Met
        1205                1210                1215

Phe Gln Leu Ala Ser Ile Gln Cys Leu Leu Ser Ser Pro Arg Lys
        1220                1225                1230

Ile Met Lys His Met Ile Glu Asn Pro Ile Leu Arg Lys Phe Trp
        1235                1240                1245

Gln Gly Glu Thr Glu Leu Tyr Asn Gln Gly Val Asn Gln Ser Lys
        1250                1255                1260

Ile Val Asn Pro Lys Lys Ile Gly Leu Glu Glu Leu His Lys Gly
        1265                1270                1275

Met Cys Gly Leu Pro Thr Val Val Gln Asn Leu Val Ile Tyr Ala
        1280                1285                1290

Lys Lys Asn Asp Ser Leu Ile Leu Gly Glu Leu Gly Tyr Pro Pro
        1295                1300                1305

Gly Asp Leu Thr Ser Asp Gly Trp Glu Ile Leu Gly Pro Gly Arg
        1310                1315                1320

Ile Pro Lys Ile Thr Asn Val Glu Ser Ala Lys Met Asp Leu Leu
        1325                1330                1335

Ser Lys Leu Met Thr Phe Leu Gly Ile Glu Ser Ser Arg Val Pro
        1340                1345                1350

Arg Thr Pro Ile His Ser Thr Arg Lys Leu Leu Lys Ile Val Arg
        1355                1360                1365

Gly Leu Glu Thr Gly Trp Gly Tyr Thr His Ala Gly Gly Ile Ser
        1370                1375                1380

Ser Ala Lys His Val Thr Gly Glu Lys Asn Leu Met Thr His Met
        1385                1390                1395

Glu Gly Arg Lys Gly Lys Tyr Ile Leu Gln Ser Gln Glu His Gly
        1400                1405                1410

Ala Asp Glu Val Glu Tyr Gly Val Lys Thr Asp Gln Arg Ala Pro
        1415                1420                1425

Asp Asn Ala Leu Cys Tyr Cys Phe Asn Pro Glu Ala Thr Asn Ile
        1430                1435                1440

Lys Gly Glu Thr Gly Ala Met Val Phe Met Lys Lys Ile Gly Lys
        1445                1450                1455

Lys Trp Thr Leu Val Thr Ser Asp Gly Asn Lys Ala Tyr Tyr Asn
        1460                1465                1470

Val Asn Asn Leu Lys Gly Trp Ser Gly Leu Pro Ile Met Leu His
        1475                1480                1485

Ser Thr Gly Ala Ile Val Gly Arg Ile Lys Ser Ala Tyr Ser Asp
        1490                1495                1500

Glu Asn Asp Leu Val Glu Glu Leu Ile Asp Ser Arg Thr Ile Ser
        1505                1510                1515

Lys Ser Asn Glu Thr Asn Leu Asn His Leu Ile Lys Glu Leu Ala
        1520                1525                1530

Asp Met Arg Arg Gly Glu Phe Arg Ser Ile Thr Leu Gly Thr Gly
        1535                1540                1545

Ala Gly Lys Thr Thr Glu Leu Pro Arg Gln Tyr Leu Thr Thr Val
        1550                1555                1560

Gly Thr His Lys Ser Val Leu Val Leu Val Pro Leu Lys Ala Pro
        1565                1570                1575
```

-continued

```
Ala Glu Ser Val Cys Arg Phe Met Arg Ser Lys Tyr Pro Thr Ile
1580                1585                1590

Asn Phe Ser Leu Arg Val Gly Glu Arg Lys Glu Gly Asp Val Ser
    1595                1600                1605

Ser Gly Ile Thr Tyr Ala Thr Tyr Gly Phe Cys Cys Gln Leu Asn
    1610                1615                1620

Leu Val Gln Leu Lys Glu Trp Ile Ser Arg Tyr Ser Met Val Phe
    1625                1630                1635

Phe Asp Glu Tyr His Thr Ala Thr Pro Glu Gln Ile Ala Ile Ile
    1640                1645                1650

Ser Lys Ile His Ala Leu Lys Val Lys Thr Arg Ile Val Ala Met
    1655                1660                1665

Ser Ala Thr Pro Pro Gly Thr Val Thr Thr Glu Gly Arg Lys Phe
    1670                1675                1680

Asp Ile Glu Glu Val Gly Val Ala Thr Ile Glu Lys Gly Glu Glu
    1685                1690                1695

Pro Lys Arg Gly Arg Val Ala Val Ala Gly Met Gln Val Pro Leu
1700                1705                1710

Glu Asp Leu Thr Gly Lys Asn Cys Leu Val Phe Val Ala Thr Lys
1715                1720                1725

Glu Ala Ala Glu Thr Glu Ala Lys Glu Leu Arg Ala Arg Gly Ile
1730                1735                1740

Asn Ala Thr Tyr Tyr Tyr Ser Gly Ile Asp Pro Lys Thr Leu Glu
1745                1750                1755

His Gly Met Thr Asn Gln Pro Tyr Cys Ile Val Ala Thr Asn Ala
1760                1765                1770

Ile Glu Ser Gly Ile Thr Cys Pro Asp Leu Asp Val Val Ile Asp
1775                1780                1785

Thr Met Gln Lys Tyr Glu Lys Val Val Asn Phe Ser Ala Lys Met
1790                1795                1800

Pro Leu Ile Val Thr Ser Leu Val Lys Lys Ile Thr Arg Glu
1805                1810                1815

Glu Gln Gly Gln Arg Lys Gly Arg Val Gly Arg Gln Lys Lys Gly
1820                1825                1830

Lys Tyr Tyr Tyr Pro Ser Gly Val Val Pro Asn Gly Ser Lys Asp
1835                1840                1845

Leu Ser Tyr Leu Ile Leu Gln Ala Gln Glu Tyr Gly Val Leu Glu
1850                1855                1860

Gln Val Asn Ile Thr Glu Tyr Phe Ile Ile Met Asn Glu Asp Trp
1865                1870                1875

Gly Leu Tyr Asp Val Asp Glu Val Glu Val Arg Ile Leu Glu Arg
1880                1885                1890

Met Asn Lys Glu Ile Leu Leu Pro Leu Gly Ile Val Glu Lys Gln
1895                1900                1905

Ile Leu Glu Arg Ser Thr His Pro Glu Lys Val Ala Leu Leu Tyr
1910                1915                1920

Asn Lys Leu Val Gln Lys Ser Pro Ile Val Tyr Pro Arg Val Gln
1925                1930                1935

Glu Gly Glu Val Ser Lys Glu Tyr Asn Thr His Asn Leu Ala Val
1940                1945                1950

Tyr Asp Lys Leu Lys Asp Val Asn Pro Gln Ala Ile Tyr Val Leu
1955                1960                1965
```

-continued

Ala Glu Glu Glu Arg Ala Thr Glu Met Met Gly Leu Glu Phe Glu
1970                1975                1980

Gln Asp Pro Ser Asp Leu Gln Asp Ser Val Val Gln Leu Cys Glu
1985                1990                1995

Asp Ile Lys Arg Tyr Thr Lys Leu Ser Gly Ile Thr Glu Lys Leu
2000                2005                2010

Leu Val Gly Thr Met Val Gly Tyr Ile Gly Tyr Lys Ala Leu Thr
2015                2020                2025

Arg Asn His Val Pro Trp Val Ser Lys Glu Tyr Cys Tyr Glu Leu
2030                2035                2040

Thr Asp Ser Pro Asp Thr Tyr Glu Asn Ser Phe Ala Pro Leu Asp
2045                2050                2055

Val Asp Ile Gln Asn Pro Gly Glu Ser Lys His Pro Glu Gln Leu
2060                2065                2070

Ala Asp His Gln Leu Arg Gln Leu Leu Glu Thr Gly Arg Asp Lys
2075                2080                2085

Ala Ile Asp Phe Leu Lys Gly Val Arg Glu Phe Thr Ser Gly Ala
2090                2095                2100

Ile Asn Ser Pro Lys Ala Leu Ser Ile Trp Glu Lys Ile Tyr Gln
2105                2110                2115

Tyr Leu Arg Lys His Gln Gly Glu Ile Ile Ser Ala Ala Trp
2120                2125                2130

Gly Ser Ala Thr Ala Leu His Asp Ser Ile Lys Ser Arg Leu Gly
2135                2140                2145

Asp Glu Val Ala Thr Ala Val Ile Ile Leu Lys Tyr Leu Ala Phe
2150                2155                2160

Gly Glu Arg Glu Leu Ser Gly Leu Thr Arg Gln Val Leu Ile Asp
2165                2170                2175

Ile Ile Val Tyr Tyr Ile Val Asn Lys Pro Arg Phe Glu Gly Asp
2180                2185                2190

Asp Tyr Ala Lys Arg Lys Gly Arg Arg Leu Val Ile Glu Val Leu
2195                2200                2205

Met Gly Ala Leu Ala Thr Tyr Ala Val Ser Asn Phe Trp Gly Val
2210                2215                2220

Ser Val Asn Lys Ile Leu Gln Pro Ile Ser Asp Tyr Leu Pro Tyr
2225                2230                2235

Ala Thr Ala Thr Leu Ala Phe Leu Arg Pro Thr Phe Met Glu Ser
2240                2245                2250

Ala Val Val Ala Ser Ser Ile Tyr Arg Ala Phe Leu Ser Ile
2255                2260                2265

Lys His Ala Glu Asn Arg Ser Leu Val Thr Gln Val Ala Ser Ala
2270                2275                2280

Ala Leu Glu Val Met Gly Leu Thr Pro Val Ser Ala Gly Leu Gly
2285                2290                2295

Val Leu Leu Gly Leu Gly Leu Cys Val Leu His Met Asn Ile Asp
2300                2305                2310

Lys Asn Glu Glu Lys Arg Thr Leu Ile Leu Lys Met Phe Val Lys
2315                2320                2325

Asn Phe Ile Asp Gln Ala Ala Leu Asp Glu Leu Asp Lys Leu Glu
2330                2335                2340

Pro Glu Lys Ile Ile Leu Ser Leu Leu Glu Gly Ile Gln Thr Cys
2345                2350                2355

Thr Asn Pro Ile Arg Ala Ile Met Ile Leu Tyr Arg Val Tyr Tyr

```
            2360                2365                2370
Lys Gly Glu Ser Phe Thr Glu Ala Leu Ser Lys Met Ala Gly Lys
            2375                2380                2385

Ser Leu Ile Val Met Val Ile Val Glu Phe Leu Glu Leu Thr Gly
            2390                2395                2400

Gln Thr Gln Gly Gly Tyr Ile Asp Leu Ser Ala Asn Leu Leu Thr
            2405                2410                2415

Phe Leu Leu Glu Lys Leu Lys Lys Met Thr Asn Leu Ala Ile Gly
            2420                2425                2430

Glu Ala Arg Lys Ala Leu Leu Pro Ile Pro Tyr Leu Tyr Cys Glu
            2435                2440                2445

Thr Trp Gln Ser Asp Ala Arg Ile Lys Ala Pro Glu Ser Tyr Asp
            2450                2455                2460

Gln Val Ala Val Glu Cys Arg Cys Gly Ala Ser Ala Arg Tyr Ser
            2465                2470                2475

Phe His His Gly Val His Glu Val Leu Glu Glu Lys Met Thr Lys
            2480                2485                2490

Trp Cys Lys Asn Phe Phe Leu Trp Gly Pro Asn Phe Ser Asn Pro
            2495                2500                2505

Asp Pro Lys Arg Met Thr Phe Tyr Glu Cys Gly Gln Ala Arg Lys
            2510                2515                2520

Cys Pro Val Ile Ile Met Gly Glu Asp Ile Thr Phe Gly Lys Tyr
            2525                2530                2535

Gly Ile Tyr Val Lys Phe His Gly Pro Asp Gly Arg Arg Leu
            2540                2545                2550

Ile Arg Gly Thr Thr His Ala Thr Ile Ser Arg Glu Glu Leu Leu
            2555                2560                2565

Glu Ile Leu Thr Ala Pro Ser Gln Val Ala Ile Gly Lys Val Lys
            2570                2575                2580

Leu Thr Asp Tyr Cys Asn Gln Lys Gly Met Ile Asp Arg Lys Leu
            2585                2590                2595

Ala Val Leu Glu Gly Asp Lys Ile His Phe Trp Lys Ala His Arg
            2600                2605                2610

Gly Ser Lys Ile Thr Asp Gln Leu Thr Ile Glu Ser Leu Thr Asp
            2615                2620                2625

Asp Leu Gly Ser Glu Ile Arg Asp Ile Thr Trp Glu Leu Tyr Thr
            2630                2635                2640

Gly Gly Thr Cys Thr Val Lys Gly Ile Ser Leu Arg Ser Cys Ala
            2645                2650                2655

Pro Gly Gln Arg Asn Lys Ala Thr Val Leu Cys Asp Cys Thr Asp
            2660                2665                2670

Val Leu Ser Pro Cys Tyr Leu Ile Asn Gly Arg Arg Pro Ser Pro
            2675                2680                2685

Phe Asp Val Val Glu Gly Tyr Glu Cys His His Arg Lys Pro Arg
            2690                2695                2700

Ala Thr Tyr Glu Asp Leu Glu Met Glu Glu Ile Leu Lys Arg Arg
            2705                2710                2715

Val Pro Val Tyr Asp Pro Leu Cys Leu Phe Asp Ile Asp Ser Lys
            2720                2725                2730

Leu Leu Pro Pro Asp Thr Tyr Leu Glu Glu Asp Arg Glu Asp
            2735                2740                2745

Phe Glu Tyr Ala Leu Arg Cys Trp Gly Leu Gly Val Tyr Val Val
            2750                2755                2760
```

-continued

Asp Gly Ser Val Thr Ser Pro Pro Asp Ile Arg Ile His His Ser
2765           2770              2775

Ser Val Leu Leu Leu Leu Thr Pro Gly Val Asp Ser Glu Leu His
2780           2785              2790

Leu Gln Tyr Ile Leu Cys Tyr Ser His Gln Ala Glu Val Asp Ile
2795           2800              2805

Tyr Ile Arg Gly Gln Leu Leu Glu Glu Glu Asn Thr Ala Thr Glu
2810           2815              2820

Ala Glu Gly Phe Gln Glu Gly Gly Asp Glu Gly Thr Gly Asp Val
2825           2830              2835

Val Ala Glu Asp Glu Asp Thr Leu Ser Thr Thr Glu Ser Ile Pro
2840           2845              2850

Pro Leu Glu Glu Glu Glu Gly Gly Gly Glu Leu Ile Thr Tyr Val
2855           2860              2865

Val Ile Arg Gly Leu Gln Glu Glu Arg Tyr Thr Ser His Leu Lys
2870           2875              2880

Leu Asn Asp Trp Ile Ser Glu Asn Ile Ser Glu Pro His Arg Val
2885           2890              2895

Gln Ile Met Leu Asp Gly Thr Val Arg Val Thr Ile Lys Glu Gly
2900           2905              2910

Lys Val Lys His Leu Phe Gly Val Tyr Arg Ile Glu Asn Ser Leu
2915           2920              2925

Glu Ala Met Phe Lys Glu Thr Ile Ala Asp Leu Pro Thr Ala Thr
2930           2935              2940

Gln Pro Pro Arg Gly Pro Ile Tyr Thr Ala Lys Glu Leu Ala Gln
2945           2950              2955

Gly Asn Ile Ala Pro Val Gln Pro Ala Ala Asn Tyr Tyr Gly Met
2960           2965              2970

Ile Glu Gly Arg Gly Asp Pro Met Thr Ala Phe Glu Ala Leu Ser
2975           2980              2985

Val Leu Arg Ser Gln Lys Val Leu Ala Lys Glu Val Lys Ile Ser
2990           2995              3000

Thr Arg Lys Ala Gln Ala Phe Leu Asn Lys Val Arg Arg Thr Ala
3005           3010              3015

Glu Ile Arg Ala Ser Glu Leu Ala Leu Lys Arg Leu Pro Val Leu
3020           3025              3030

Gly Lys Ile Asn Gly Arg Lys Leu Ile Arg Glu Glu Thr Asn Ile
3035           3040              3045

Pro Asn Gln Arg Leu Ala Ser Ile Met Thr Ser Ile Gly Ile Arg
3050           3055              3060

Leu Glu Lys Leu Pro Val Val Arg Ala Asn Thr Ser Gly Pro Lys
3065           3070              3075

Phe Arg Gln Ser Ile Leu Glu Lys Met Asp Lys Tyr Glu Asn Glu
3080           3085              3090

Gln Val Pro Glu Leu His Glu Lys Met Trp Ala Ala Phe Leu Val
3095           3100              3105

Thr Ala Arg Gln Asp Leu Arg Asn Thr Tyr Glu Glu Val Thr Tyr
3110           3115              3120

Pro Glu Leu Glu Ile Gly Ile Asn Arg Lys Gly Ala Pro Gly Phe
3125           3130              3135

Phe Glu Lys Glu Ser Ser Ile Gly Glu Val Leu Glu Lys Lys Glu
3140           3145              3150

Lys Ile Asp Val Val Ile Arg Glu Ile Glu Lys Gly Thr His Leu
3155             3160                 3165

Tyr Tyr Glu Thr Ala Met Pro Lys Asn Glu Lys Arg Asp Val Leu
3170             3175                 3180

Asp Asp Trp Leu Ser Glu Asp Phe Val Thr Tyr Lys Lys Pro Arg
3185             3190                 3195

Val Ile Gln Tyr Pro Glu Ala Val Thr Arg Leu Ala Ile Thr Lys
3200             3205                 3210

Ile Met Tyr Lys Trp Val Lys Gln Lys Pro Val Val Ile Pro Gly
3215             3220                 3225

Tyr Glu Gly Lys Thr Pro Ile Phe Glu Ile Phe Glu Lys Val Ser
3230             3235                 3240

Ala Asp Trp Ala Gln Phe Lys Asn Pro Val Ala Val Ser Phe Asp
3245             3250                 3255

Thr Arg Ala Trp Asp Thr Gln Val Thr Arg Glu Asp Leu Lys Leu
3260             3265                 3270

Val Gly Arg Ile Gln Lys Tyr Tyr Tyr Lys Lys Lys Tyr Trp Lys
3275             3280                 3285

Phe Ile Asp Asn Leu Thr Thr Met Met Glu Glu Val Pro Val Ile
3290             3295                 3300

Thr Val Glu Gly Asp Met Phe Leu Arg Val Gly Gln Arg Gly Ser
3305             3310                 3315

Gly Gln Pro Asp Thr Ser Ala Gly Asn Ser Ile Leu Asn Val Leu
3320             3325                 3330

Thr Met Leu Val Ala Phe Ser Glu Ser Thr Asn Leu Pro Ile Ala
3335             3340                 3345

Ala Ala Trp Arg Ala Cys Arg Ile His Val Cys Gly Asp Asp Gly
3350             3355                 3360

Phe Leu Ile Thr Glu Ser Glu Leu Gly Arg Lys Phe Ala Glu Lys
3365             3370                 3375

Gly Val Pro Leu Leu Ala Ser Phe Gly Lys Pro Gln Lys Ile Thr
3380             3385                 3390

Glu Gly Ala Ser Leu Lys Ile Thr Ser Asn Phe Asp Gly Ile Glu
3395             3400                 3405

Phe Cys Ser His Ser Pro Ile Arg Val Gln Thr Pro Asn Ile Arg
3410             3415                 3420

Trp Met Pro Ala Arg Pro Thr Ala Thr Ile Leu Gly Lys Met Ser
3425             3430                 3435

Thr Arg Leu Gly Glu Gly Ala Thr Arg Ser Gly Glu Glu Tyr Glu
3440             3445                 3450

Lys Gln Val Ala Phe Ala Tyr Leu Leu Met Tyr Pro Trp Asn Pro
3455             3460                 3465

Leu Ile Arg Arg Ile Gly Leu Leu Leu Ser Thr Thr Asp Pro
3470             3475                 3480

Met Gly Lys Glu Glu Thr Pro Cys Ser Asp Glu Gly Val Lys Tyr
3485             3490                 3495

Val Gly Asp Pro Ile Ala Ala Tyr Arg Asp Val Trp Gly His Lys
3500             3505                 3510

Leu Glu Asp Val Gly His Val Asp Gln Ser Gln Leu Ser Arg Met
3515             3520                 3525

Asn Tyr Ser Met Thr Tyr Leu Gly Ile Trp Lys Pro Lys Thr Ser
3530             3535                 3540

Gln Arg Leu Val Glu Gln Cys Cys Arg Leu Ala Glu Lys Asn Asn

```
              3545                3550                3555

Cys Val Ala Arg Ala Asp Ser Leu Ile Lys Lys Val Lys Ile
              3560                3565                3570

Thr Tyr Asp Pro Gly Ile Gly Ala Ala Gln Val Ile Arg Arg Trp
              3575                3580                3585

Glu Glu Leu Glu Trp Thr Arg Arg Lys Pro Glu Phe Thr Lys Val
              3590                3595                3600

Thr Ala Glu Asp Asp Leu Phe Leu Val Leu Phe Lys Arg Leu Ser
              3605                3610                3615

Lys Tyr Ile Phe Gln Lys Ile Lys Phe Met Gln Lys Met Phe Thr
              3620                3625                3630

Pro Tyr
              3635

<210> SEQ ID NO 3
<211> LENGTH: 624
<212> TYPE: DNA
<213> ORGANISM: Porcine pestivirus 1 strain 000515
<220> FEATURE:
<221> NAME/KEY: Erns gene
<222> LOCATION: (1)..(624)

<400> SEQUENCE: 3
aaggtccagt ggttttttaaa ggatgaaaat tcgtcaggaa ttaaccaggt attatggaga      60
agacagatca acagatccct acatggggag tggcctaacc agatttgcca tggcatgcca     120
aatgaaacta tcactgacga ggaattacgc agtttaggaa tgatagatac aagccctaga     180
acaaactata cttgctgtca gttgcaatat catgaatgga gaaaacatgg ttggtgcaat     240
tacccacaaa aacaggcttg gatcaggaga atagcgaccc tgcaagccaa cctcaccgga     300
gcttataagg gacctgagtg tgctgtcatc tgtcgattta acggcaccta taacattgtg     360
agacaggcca gagacgaggt gagtccactg acagggtgta aggaagggca ccctttttcta    420 ttttctgagg aaaggtccga cacctcgtgc ttgaggccgc cctccactag ttgggtgaga     480
ccagtgaaaa tggatgaggc atcgatggct gacagcttcg cccacggggt cgataaggcc     540
ataatattaa tcagaaaagg ggcatcggga attatcaatt tcctagacac tattgggaga     600
tggttaccgg tgactgaagc agct                                             624

<210> SEQ ID NO 4
<211> LENGTH: 208
<212> TYPE: PRT
<213> ORGANISM: Porcine pestivirus 1 strain 000515
<220> FEATURE:
<221> NAME/KEY: MISC_FEATURE
<222> LOCATION: (1)..(208)
<223> OTHER INFORMATION: Erns protein

<400> SEQUENCE: 4

Lys Val Gln Trp Phe Leu Lys Asp Glu Asn Ser Ser Gly Ile Asn Gln
 1               5                  10                  15

Val Leu Trp Arg Arg Gln Ile Asn Arg Ser Leu His Gly Glu Trp Pro
                20                  25                  30

Asn Gln Ile Cys His Gly Met Pro Asn Glu Thr Ile Thr Asp Glu Glu
            35                  40                  45

Leu Arg Ser Leu Gly Met Ile Asp Thr Ser Pro Arg Thr Asn Tyr Thr
        50                  55                  60

Cys Cys Gln Leu Gln Tyr His Glu Trp Lys Lys His Gly Trp Cys Asn
65                  70                  75                  80
```

Tyr Pro Gln Lys Gln Ala Trp Ile Arg Arg Ile Ala Thr Leu Gln Ala
            85                  90                  95

Asn Leu Thr Gly Ala Tyr Lys Gly Pro Glu Cys Ala Val Ile Cys Arg
        100                 105                 110

Phe Asn Gly Thr Tyr Asn Ile Val Arg Gln Ala Arg Asp Glu Val Ser
    115                 120                 125

Pro Leu Thr Gly Cys Lys Glu Gly His Pro Phe Leu Phe Ser Glu Glu
130                 135                 140

Arg Ser Asp Thr Ser Cys Leu Arg Pro Pro Ser Thr Ser Trp Val Arg
145                 150                 155                 160

Pro Val Lys Met Asp Glu Ala Ser Met Ala Asp Ser Phe Ala His Gly
            165                 170                 175

Val Asp Lys Ala Ile Ile Leu Ile Arg Lys Gly Ala Ser Gly Ile Ile
        180                 185                 190

Asn Phe Leu Asp Thr Ile Gly Arg Trp Leu Pro Val Thr Glu Ala Ala
    195                 200                 205

<210> SEQ ID NO 5
<211> LENGTH: 22
<212> TYPE: DNA
<213> ORGANISM: Artificial Sequence
<220> FEATURE:
<223> OTHER INFORMATION: Synthetic primer

<400> SEQUENCE: 5
tttagacacg acccctcagc cc                                            22

<210> SEQ ID NO 6
<211> LENGTH: 21
<212> TYPE: DNA
<213> ORGANISM: Artificial Sequence
<220> FEATURE:
<223> OTHER INFORMATION: Synthetic primer

<400> SEQUENCE: 6
ccacttgccc attatagacc g                                             21

<210> SEQ ID NO 7
<211> LENGTH: 22
<212> TYPE: DNA
<213> ORGANISM: Artificial Sequence
<220> FEATURE:
<223> OTHER INFORMATION: Synthetic primer

<400> SEQUENCE: 7
ttatggtgcc tgttactgtc tg                                            22

<210> SEQ ID NO 8
<211> LENGTH: 21
<212> TYPE: DNA
<213> ORGANISM: Artificial Sequence
<220> FEATURE:
<223> OTHER INFORMATION: Synthetic primer

<400> SEQUENCE: 8
acctcgtctc tggcctgtct c                                             21

<210> SEQ ID NO 9
<211> LENGTH: 19
<212> TYPE: DNA
<213> ORGANISM: Artificial Sequence
<220> FEATURE:

```
<223> OTHER INFORMATION: Synthetic primer

<400> SEQUENCE: 9
agtgtgctgt catctgtcg                                           19

<210> SEQ ID NO 10
<211> LENGTH: 21
<212> TYPE: DNA
<213> ORGANISM: Artificial Sequence
<220> FEATURE:
<223> OTHER INFORMATION: Synthetic primer

<400> SEQUENCE: 10
cttccttaca ccctgtcagt g                                        21
```